US010603017B2

(12) United States Patent
Takayama et al.

(10) Patent No.: US 10,603,017 B2
(45) Date of Patent: Mar. 31, 2020

(54) ULTRASOUND DIAGNOSTIC APPARATUS AND BIOMEDICAL EXAMINATION APPARATUS

(71) Applicant: KABUSHIKI KAISHA TOSHIBA, Minato-ku (JP)

(72) Inventors: Satoshi Takayama, Kawasaki (JP); Taeko Urano, Kawasaki (JP); Kenji Nakamura, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 411 days.

(21) Appl. No.: 15/265,175

(22) Filed: Sep. 14, 2016

(65) Prior Publication Data

US 2017/0258453 A1   Sep. 14, 2017

(30) Foreign Application Priority Data

Mar. 14, 2016 (JP) .................................. 2016-049992

(51) Int. Cl.
*A61B 8/08* (2006.01)
*A61B 5/00* (2006.01)
(Continued)

(52) U.S. Cl.
CPC .......... *A61B 8/5261* (2013.01); *A61B 5/0059* (2013.01); *A61B 8/14* (2013.01); *A61B 8/4416* (2013.01)

(58) Field of Classification Search
USPC ...................................................... 600/443
See application file for complete search history.

(56) References Cited

U.S. PATENT DOCUMENTS 6,015,969 A *   1/2000  Nathel ................. G01N 21/314
                                                       250/227.27
2004/0215072 A1* 10/2004  Zhu ...................... A61B 5/0091
                                                       600/407
(Continued)

FOREIGN PATENT DOCUMENTS

JP   2000-237196 A   9/2000
JP   2005-331292 A   12/2005
(Continued)

OTHER PUBLICATIONS

Rafael C. Gonzales and Richard E. Woods, Digital Image Processing, Jun. 1992, ISBN 0-201-50803-6 p. 213-218 (Year: 1992).*
(Continued)

*Primary Examiner* — Amelie R Davis
*Assistant Examiner* — John Denny Li
(74) *Attorney, Agent, or Firm* — Oblon, McClelland, Maier & Neustadt, L.L.P.

(57) ABSTRACT

According to one embodiment, an ultrasound diagnostic apparatus comprises processing circuitry. The processing circuitry sets one of wavelengths of a plurality of light sources as a reference wavelength, normalize an intensity of light having a wavelength other than the reference wavelength, which is detected by a pair of each light irradiation unit and each optical detector, with an intensity of light having the reference wavelength, calculate a first value for each pair by nonlinear enhancement correction of a normalized light intensity, calculate a second value for the each pair by nonlinear reduction correction of an intensity of light having the reference wavelength detected by the each pair, and calculate an evaluation value based on a value obtained by multiplication of the first value and the second value for the each pair.

12 Claims, 15 Drawing Sheets

(51) Int. Cl.
*A61B 8/14* (2006.01)
*A61B 8/00* (2006.01)

(56) References Cited

U.S. PATENT DOCUMENTS

| | | | |
|---|---|---|---|
| 2006/0184050 A1* | 8/2006 | Urano | A61B 5/0073 600/485 |
| 2008/0058638 A1 | 3/2008 | Zhu et al. | |
| 2009/0069653 A1 | 3/2009 | Yoshida et al. | |
| 2010/0094134 A1 | 4/2010 | Zhu et al. | |
| 2011/0268362 A1 | 11/2011 | Toma et al. | |
| 2013/0253322 A1 | 9/2013 | Suzuki et al. | |
| 2015/0305712 A1 | 10/2015 | Urano et al. | |
| 2016/0270662 A1 | 9/2016 | Takayama et al. | |
| 2016/0270765 A1 | 9/2016 | Takayama et al. | |

FOREIGN PATENT DOCUMENTS

| | | |
|---|---|---|
| JP | 2007-20735 A | 2/2007 |
| JP | 2008-79835 A | 4/2008 |
| JP | 2009-77931 A | 4/2009 |
| JP | 2009-232876 A | 10/2009 |
| JP | 2012-85965 A | 5/2012 |
| JP | 5219440 B2 | 6/2013 |
| JP | 2014-110878 A | 6/2014 |
| JP | 2014-239815 A | 12/2014 |
| JP | 2015-123252 A | 7/2015 |
| JP | 2016-64113 A | 4/2016 |
| JP | 2016-171909 A | 9/2016 |
| JP | 2016-171910 A | 9/2016 |
| JP | 2017-55866 A | 3/2017 |
| WO | WO 2011/027548 A1 | 3/2011 |

OTHER PUBLICATIONS

Quing Zhu, et al., "Benign versus Malignant Breast Masses: Optical Differentiation with US-guided Optical Imaging Reconstruction", Radiology, vol. 237, 2005, pp. 57-66.

Nan Guang Ghen, et al., "Simultaneous near-infrared diffusive light and ultrasound imaging", Applied Optics, vol. 40, No. 34, 2001, pp. 6367-6380.

* cited by examiner

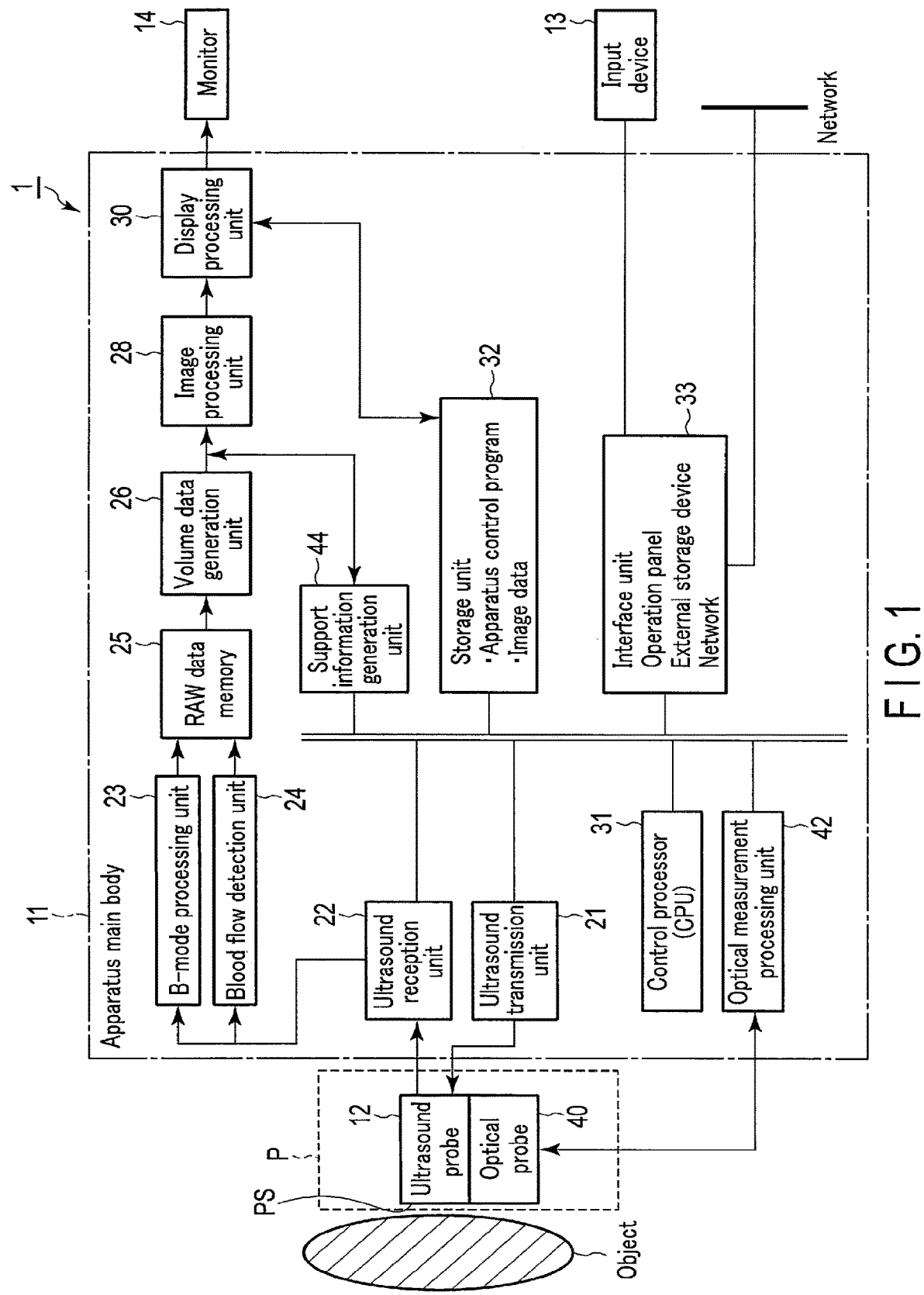
F I G. 1

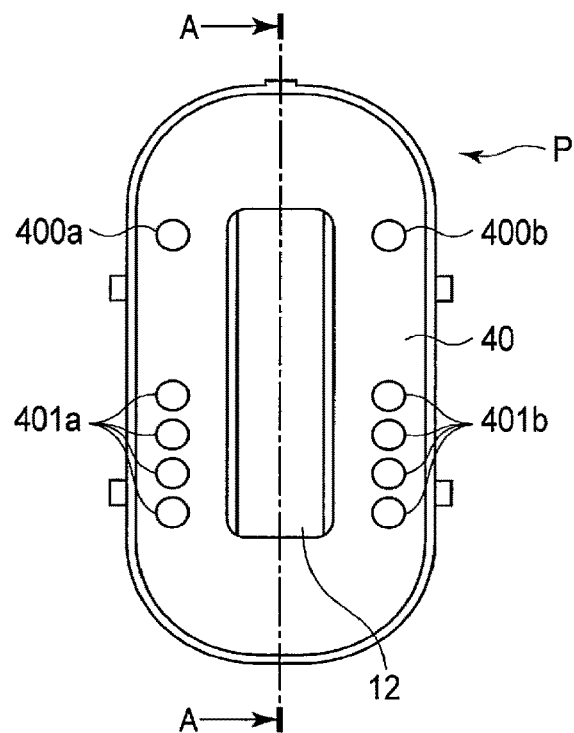
F I G. 2
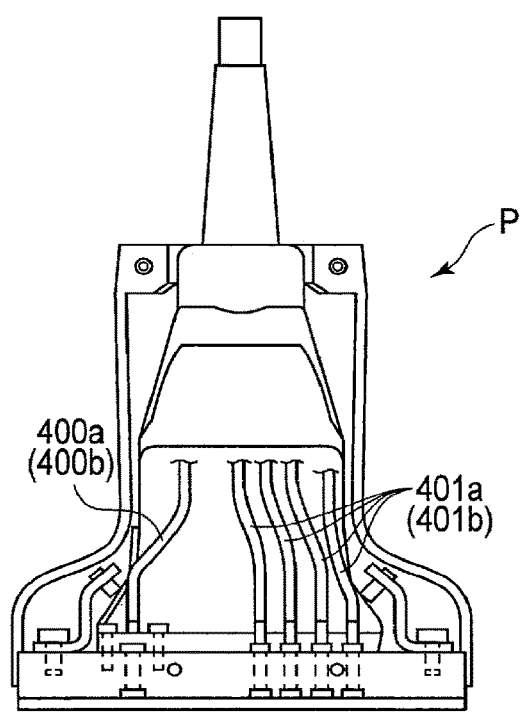
F I G. 3

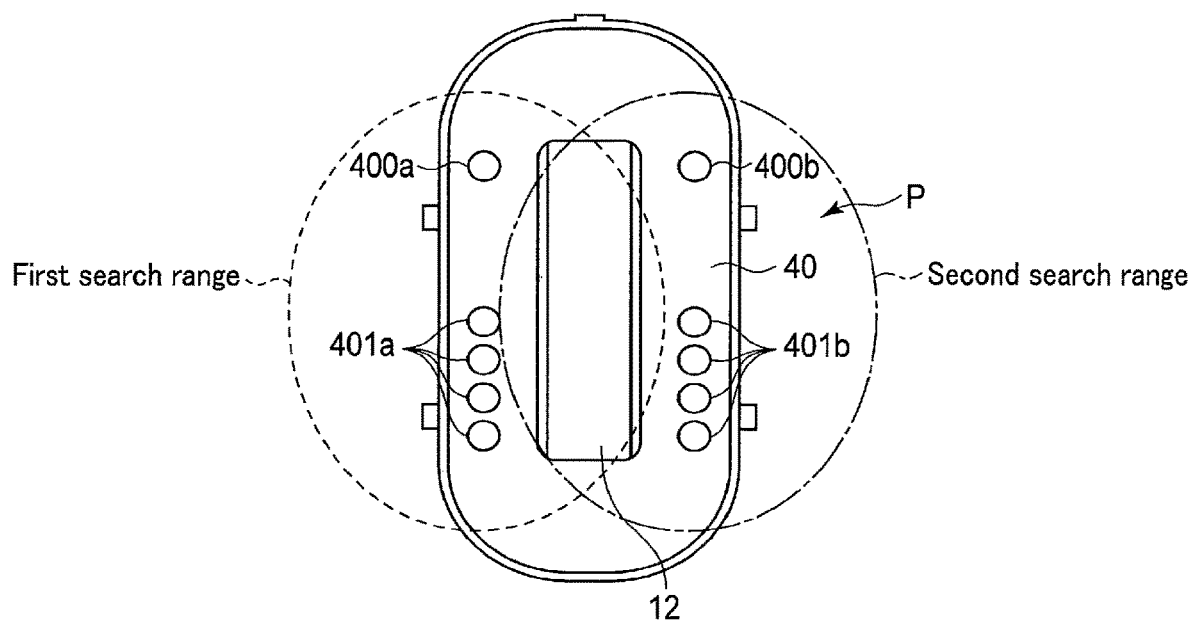
F I G. 6A
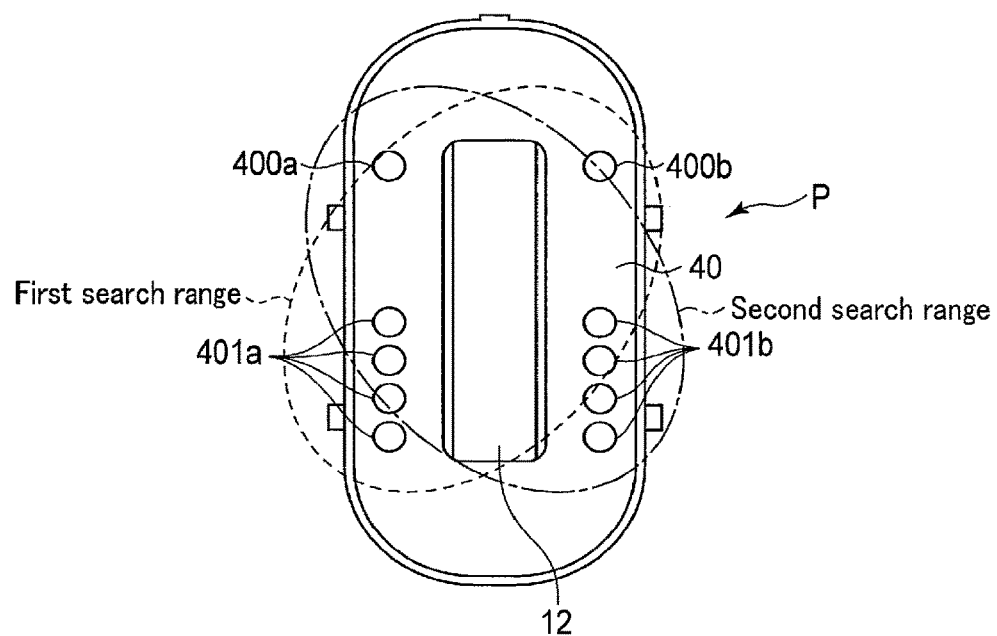
F I G. 6B

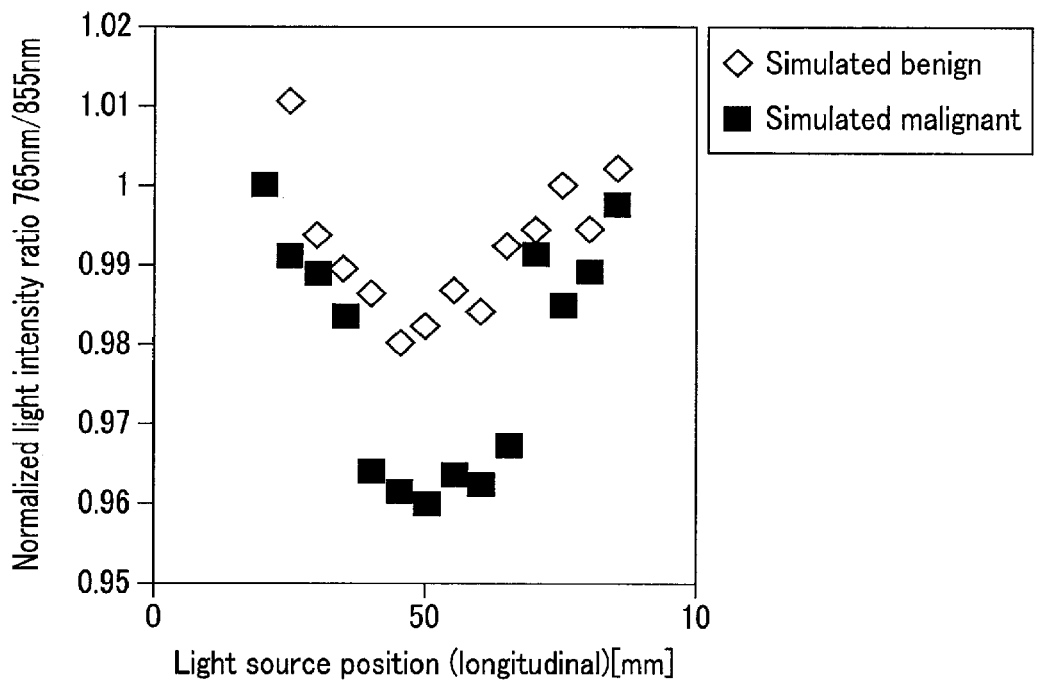
Light intensity ratio
F I G. 7A
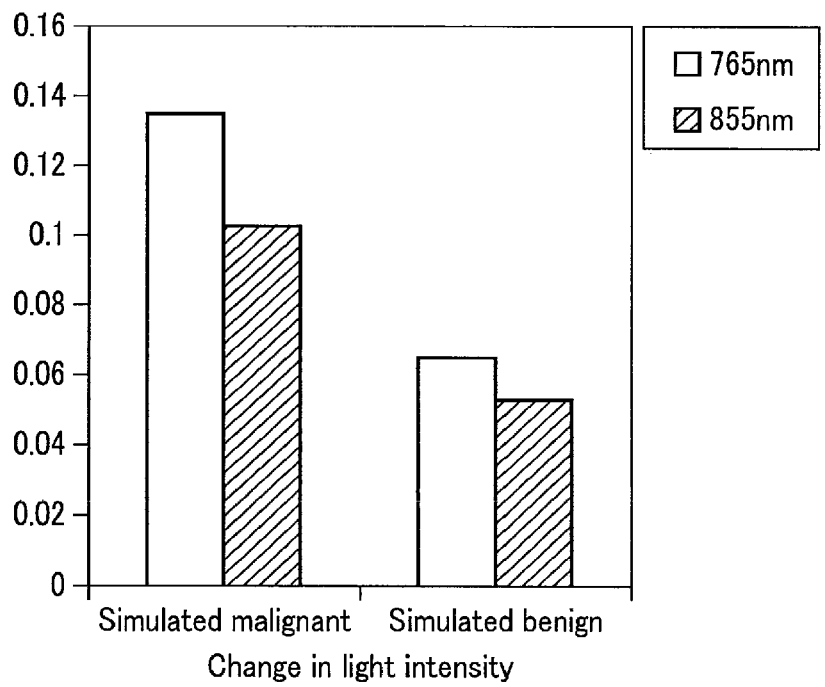
Change in light intensity
F I G. 7B

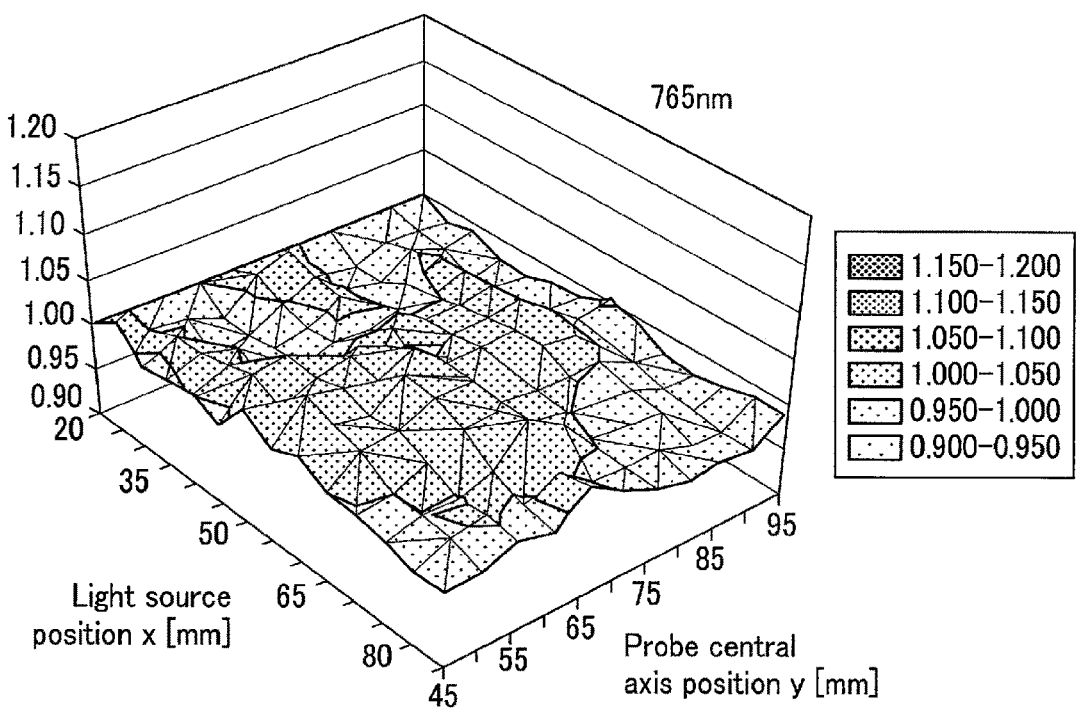
F I G. 11
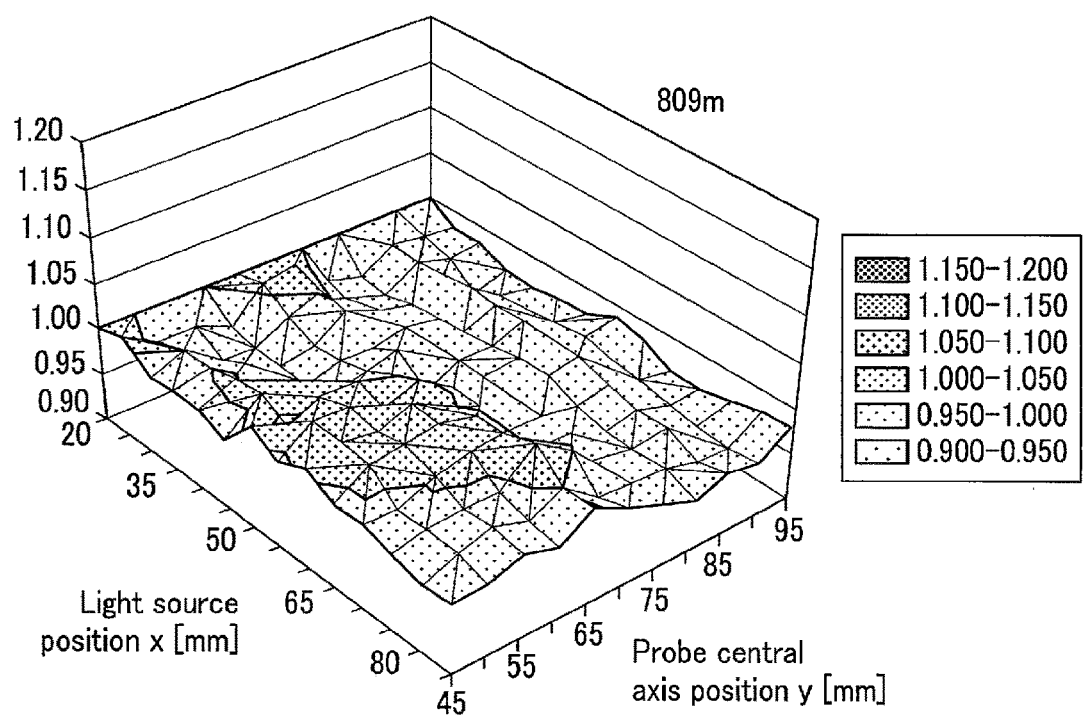
F I G. 12

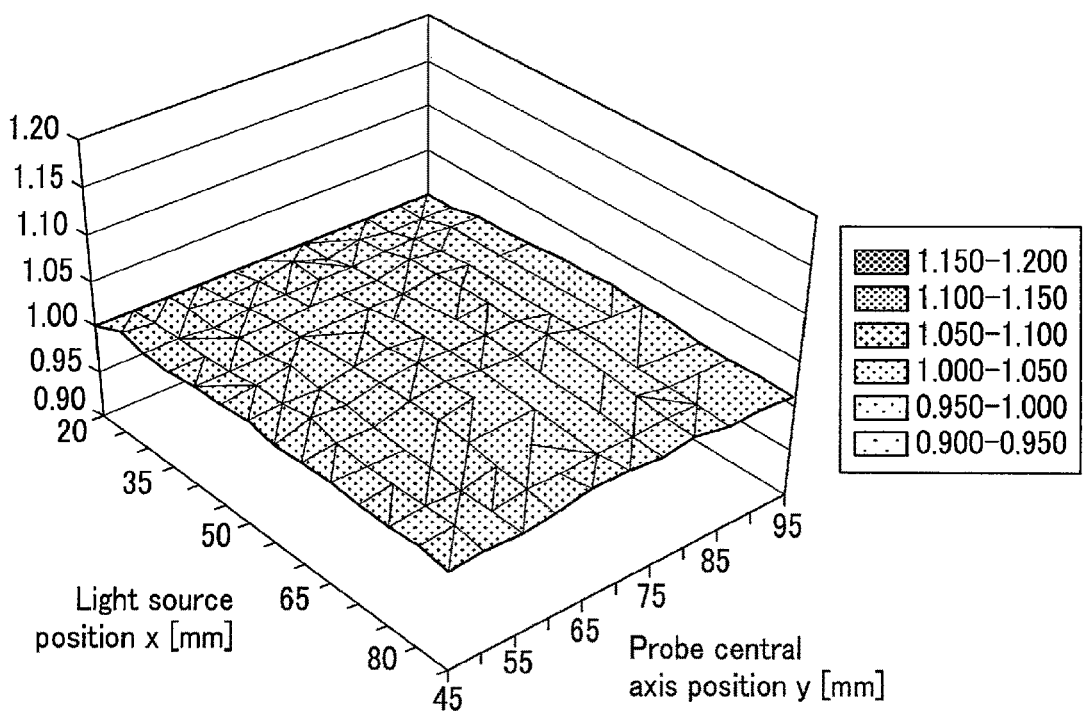
F I G. 13
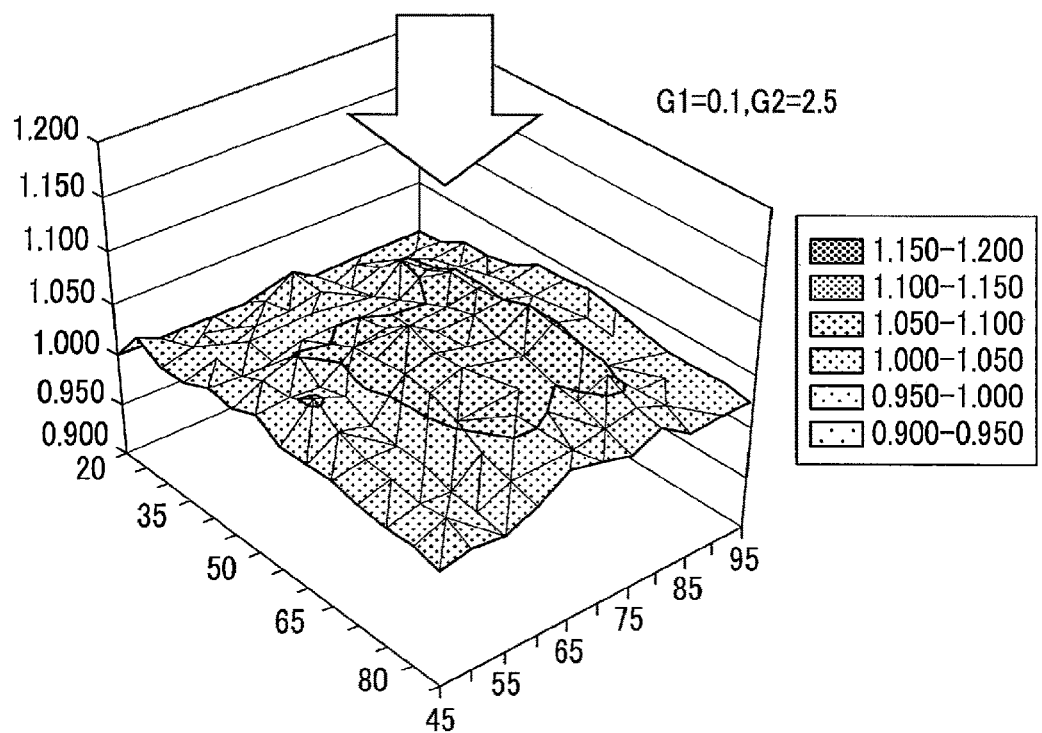
F I G. 14

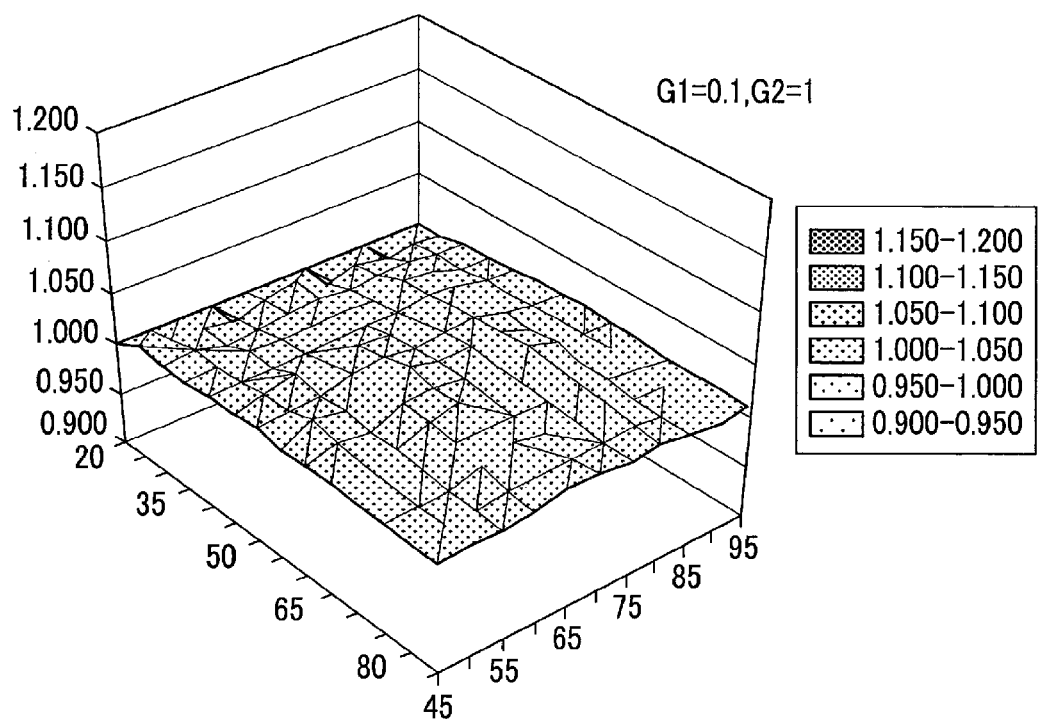
F I G. 15
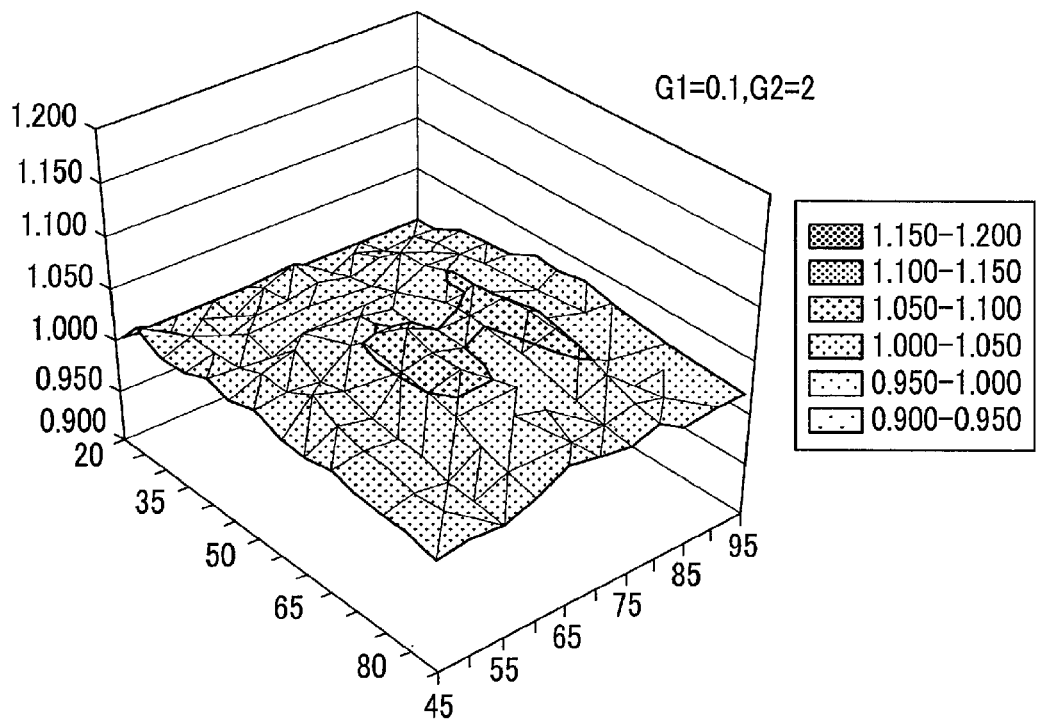
F I G. 16

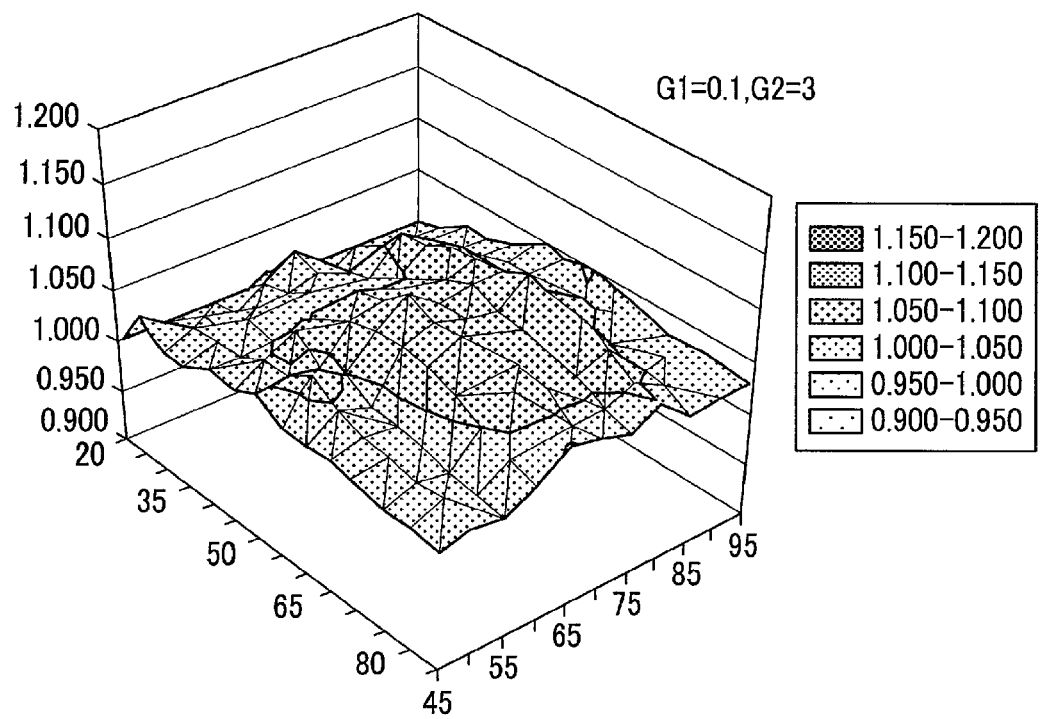
F I G. 17
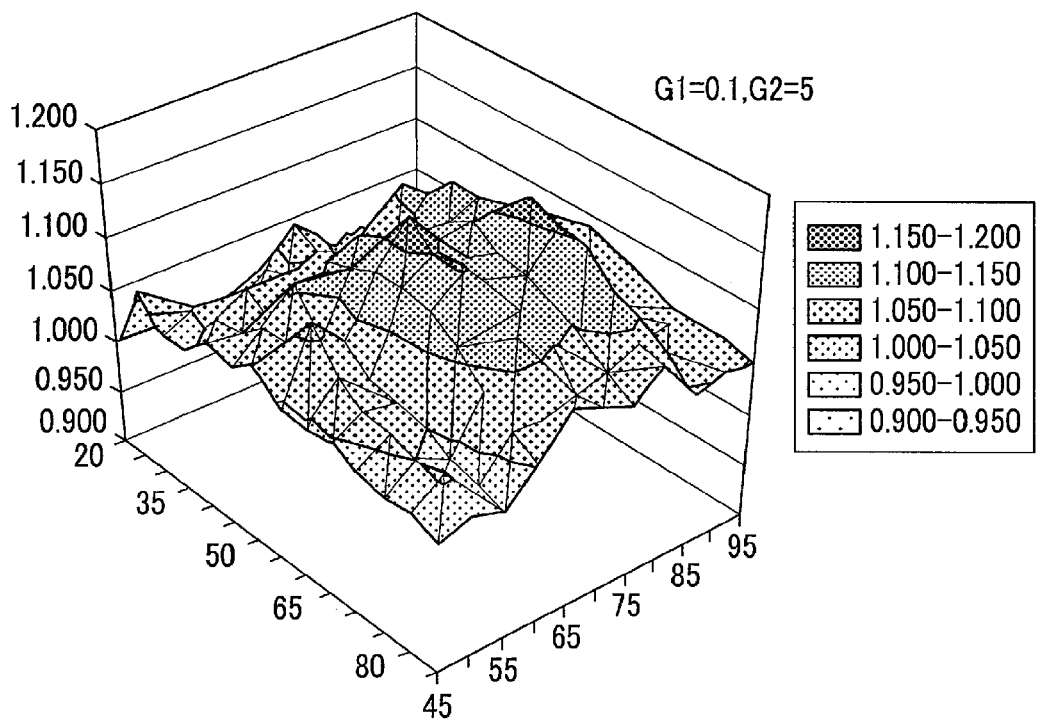
F I G. 18

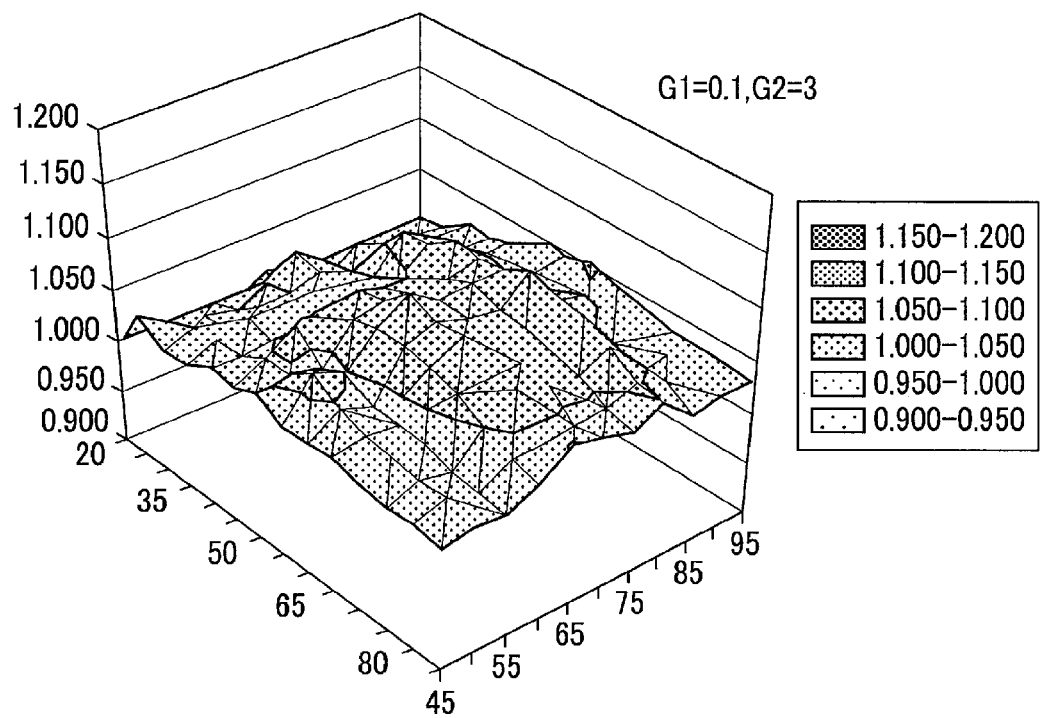
F I G. 19
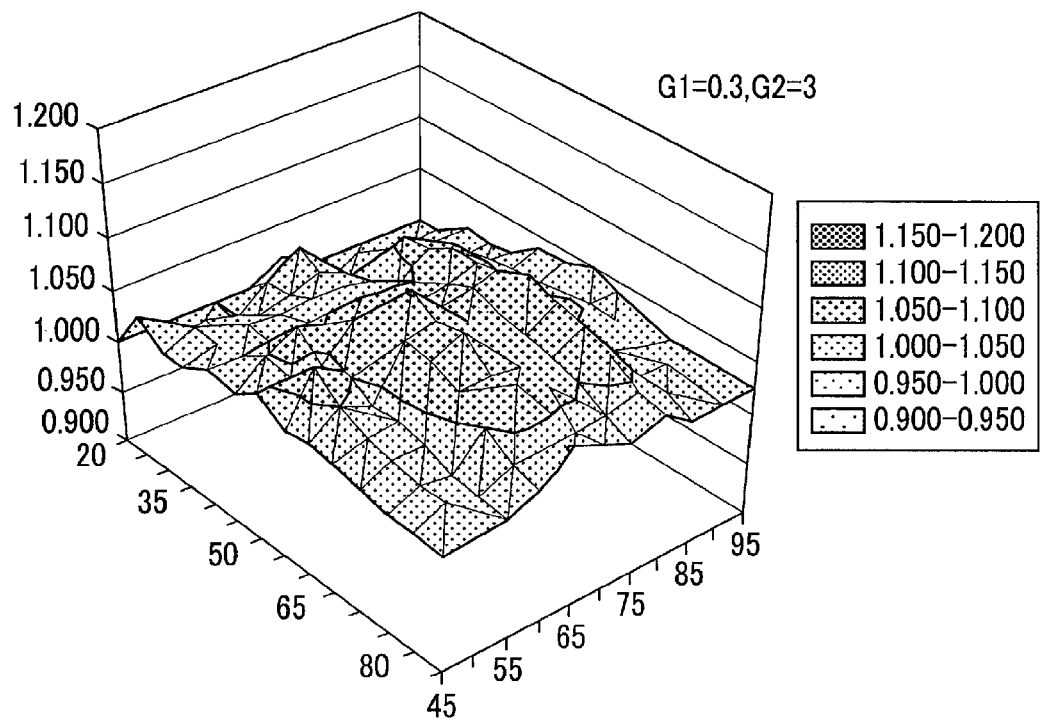
F I G. 20

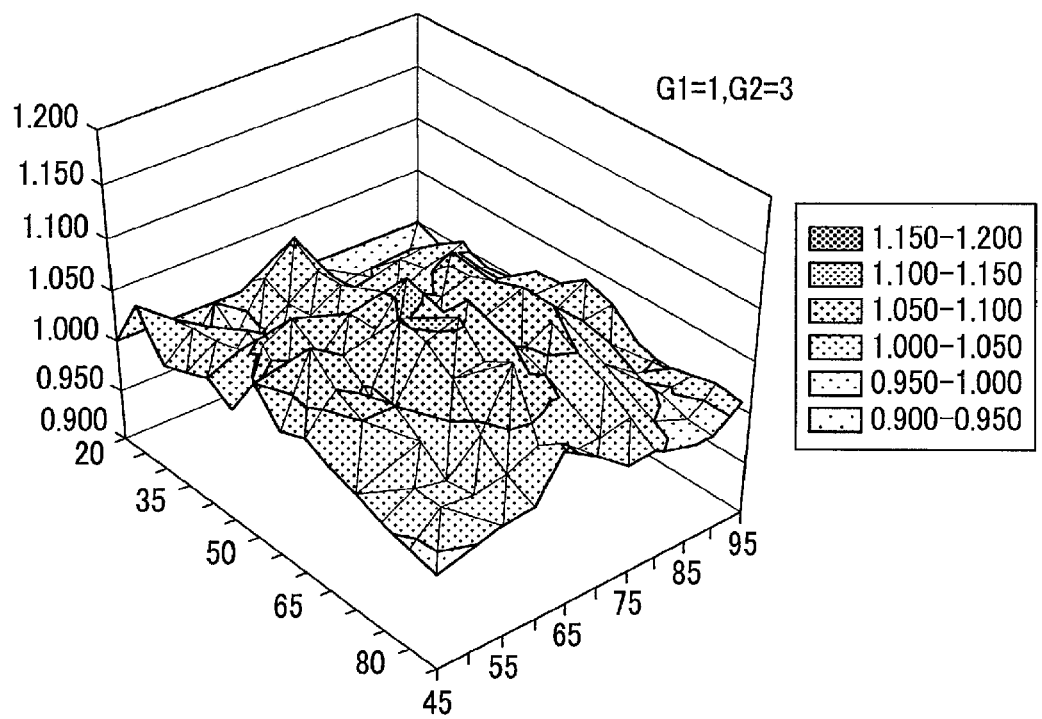
F I G. 23
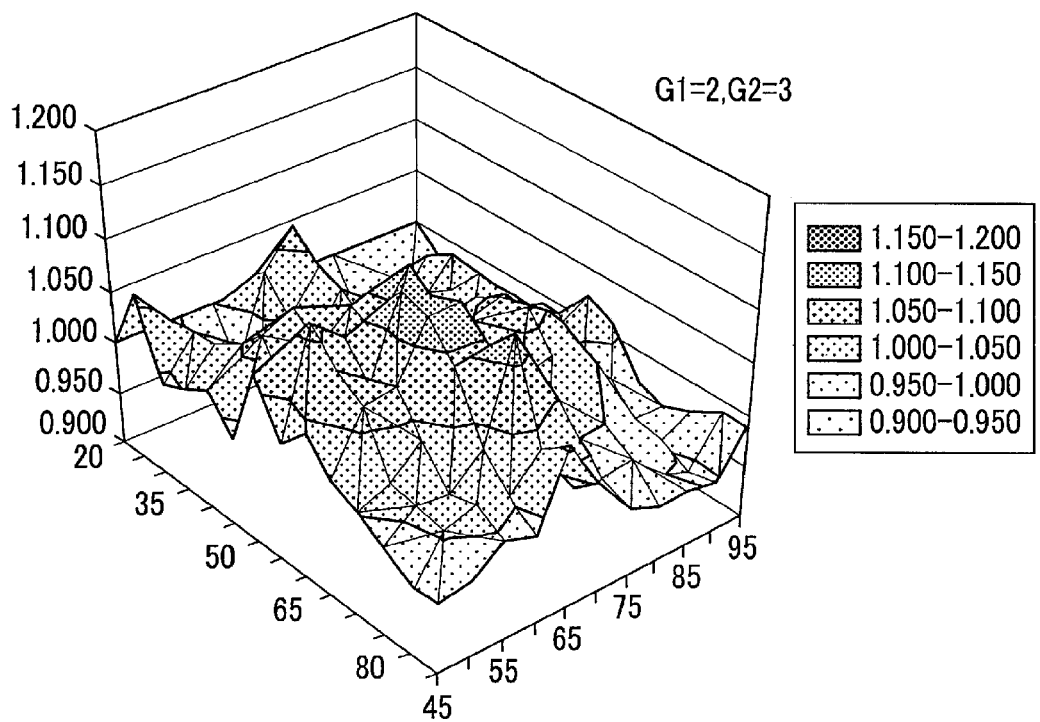
F I G. 24

ULTRASOUND DIAGNOSTIC APPARATUS AND BIOMEDICAL EXAMINATION APPARATUS

CROSS-REFERENCE TO RELATED APPLICATIONS

This application is based upon and claims the benefit of priority from the prior Japanese Patent Application No. 2016-049992, filed Mar. 14, 2016 the entire contents which are incorporated herein by reference.

FIELD

Embodiments described herein relate generally to an ultrasound diagnostic apparatus and a biomedical examination apparatus.

BACKGROUND

Embodiments described herein relate generally to an ultrasound diagnostic apparatus and a biomedical examination apparatus.

Breast cancer is one of the causes of women death. Breast cancer screening and early diagnosis have very high values in terms of reducing mortality rate and suppressing the cost of health care.

Existing methods include palpation of breast tissues and X ray imaging for searching for suspected tissue deformation. If there is a suspected portion in an X ray photograph, ultrasound imaging is performed, and surgical tissue examination is further performed. A series of these examinations require much time to reach a final conclusion. In addition, since premenopausal young women have many mammary glands, high sensitivity is difficult to obtain in X ray imaging. Therefore, screening using ultrasound imaging has great significance for the young generation, in particular.

In general, in ultrasound imaging, a certified operator acquires ultrasound images, and an expert interpreter (a plurality of interpreters in some cases) makes determination from morphological information on the images. When performing medical examination, the maximum number of persons subjected to screening per operator per day is 50 in consideration of the risk of oversights caused by the fatigue and lack of concentration of the operator.

In order to acquire a still image capturing a morphological characteristic in ultrasound imaging, it is very important for the operator to have knowledge and experience. High skill is also required to perform accurate and quick screening. For example, standard examination times per object are 5 to 10 min. However, it sometimes takes more time for screening depending on the skill of an operator. That is, in screening based on current ultrasound imaging, the accuracy of image acquisition may vary depending on the levels of skill of operators. When acquiring images, the operator needs to keep paying close attention to images. Besides, he/she takes charge of making determination by himself/herself, and hence a heavy mental strain is imposed on him/her even if he/she is a skilled operator. Although there is available a scheme of acquiring all image information from a moving image, there is no established technique for automatic search using image recognition. For this reason, an interpreter searches a moving image for still images. In this case, a heavy burden is imposed on the interpreter.

In order to solve the above problem, the present applicant has proposed an apparatus with the concept of complement of ultrasound echo diagnosis by using a compact optical examination system designed to reduce a burden on a technician by guiding the measurement position of an ultrasound echo probe in a plane direction based on the metabolic information of the living body which is obtained by optical measurement. FIG. 18 shows the light absorption spectra of oxygenated hemoglobin and deoxygenated hemoglobin. In general, deoxygenated hemoglobin ratio in a malignant tumor region is higher in ratio than in a healthy region, and hence an analysis result on the absorption of deoxygenated hemoglobin is one of the bases for determining the degree malignancy of a target region in optical biomedical examination. The wavelength regions of light suitable for the light absorption measurement of deoxygenated hemoglobin are 740 nm to 790 nm in the near infrared light region and 650 nm to 690 nm in the red light region. The wavelength region of light suitable for the light absorption measurement of oxygenated hemoglobin is 830 nm to 900 nm in the near infrared light region. The wavelength region of light to identify a total hemoglobin amount is, for example, 800 nm to 820 nm in the near infrared light region. Specific light sources include an LED and an LD. In consideration of absorption wavelength of other biological components such as water, fat, and melanin and biodistributions, an output light intensity and a half width must be properly selected for a light source.

As a method of effectively detecting a suspected position in a breast cancer detection technique, there has also been proposed a method using a plurality of light sources having peaks at different wavelengths corresponding to the light absorption of oxygenated hemoglobin and deoxygenated hemoglobin. This method detects abnormal absorption based on a value (light intensity ratio) obtained by normalizing the light intensity of one light source with the light intensity of the other light source. In a normal region of the breast, since there is no difference in oxygen saturation in blood, normalized light intensities are almost constant. In contrast to this, a malignant tumor region such as a breast cancer region is higher in blood density and lower in oxygen saturation than the surrounding region, and hence it is possible to detect a difference in normalized light intensity. Detecting a normalized light intensity difference makes it possible to implement navigation to a suspected position (the position of an abnormal region or suspected abnormal region) or feedback to a precise measurement position at the time of automatic measurement.

As described above, normalized light intensities are effective for the navigation of a probe to a suspected position. On the other hand, in order to derive a light absorption coefficient in each region, it is necessary to perform analysis of each wavelength. When, for example, quantifying the oxygen saturation of a suspected cancer region, it is necessary to perform analysis to derive light absorption coefficients with respect to near-infrared wavelengths corresponding to oxygenated hemoglobin and deoxygenated hemoglobin. For this reason, normalized light intensities cannot be used for the quantification of oxygen saturations.

On the other hand, a serious problem in the actual measurement of the living body is a shift/variation in measurement light intensity caused by pressing and relaxing of a probe. The present inventors have solved this problem by performing the correction processing of performing normalization with a reference light source of a wavelength near to a measurement wavelength.

In general, however, the light intensity ratio difference between a healthy region and a suspected region is small. For this reason, using light intensity ratios sometimes makes it impossible to perform satisfactory appearance determination concerning a suspected region, and hence further improvements are demanded.

It is an object of an embodiment to provide an ultrasound diagnostic apparatus and living body examination apparatus which can accurately guide an optical ultrasound probe to a body surface portion corresponding to a suspected region when measuring light intensities by bringing the optical ultrasound probe into contact with the object.

BRIEF DESCRIPTION OF THE DRAWING

FIG. 1 is a block diagram showing the arrangement of an ultrasound diagnostic apparatus 1 according to an embodiment;

FIG. 2 is a view showing a probe P when viewed from the contact surface side with an object;

FIG. 3 is a sectional view taken along A-A in FIG. 2 when viewed from the arrow direction;

FIG. 6A is a view for explaining optical measurement processing complying with a rough search mode, and FIG. 6B is view for explaining optical measurement processing complying with a fine adjustment mode;

FIG. 7A is a graph showing the spatial distribution of normalized light intensity ratios with respect to a simulated benign tumor and a simulated malignant tumor, and FIG. 7B is a graph showing light intensities with respect to the benign and the malignant;

FIG. 11 is a graph showing the spatial distribution of values obtained by normalizing light intensities measured using light having wavelength $\lambda 1=765$ nm with an initial value at the time of optical measurement of a phantom;

FIG. 12 is a graph showing the spatial distribution of values obtained by normalizing light intensities measured using light having wavelength $\lambda 0=809$ nm with an initial value at the time of optical measurement of a phantom;

FIG. 13 is a graph showing the spatial distribution of values obtained by normalizing normalized $\lambda 0$ intensities with normalized $\lambda 1$ intensities at the time of optical measurement of a phantom;

FIG. 14 is a graph showing the spatial distribution of proximity evaluation values at the time of optical measurement of a phantom;

FIG. 15 is a graph showing the distribution of proximity evaluation values when weight indices G1 and G2 are set to (0.1, 1);

FIG. 16 is a graph showing the distribution of proximity evaluation values when the weight indices G1 and G2 are set to (0.1, 2);

FIG. 17 is a graph showing the distribution of proximity evaluation values when the weight indices G1 and G2 are set to (0.1, 3);

FIG. 18 is a graph showing the distribution of proximity evaluation values when the weight indices G1 and G2 are set to (0.1, 5);

FIG. 19 is a graph showing the distribution of proximity evaluation values when the weight indices G1 and G2 are set to (0.1, 3);

FIG. 20 is a graph showing the distribution of proximity evaluation values when the weight indices G1 and G2 are set to (0.3, 3);

FIG. 23 is a graph showing the distribution of proximity evaluation values when the weight indices G1 and G2 are set to (1, 3); and FIG. 24 is a graph showing the distribution of proximity evaluation values when the weight indices G1 and G2 are set to (2, 3).

DETAILED DESCRIPTION

Figure 4:
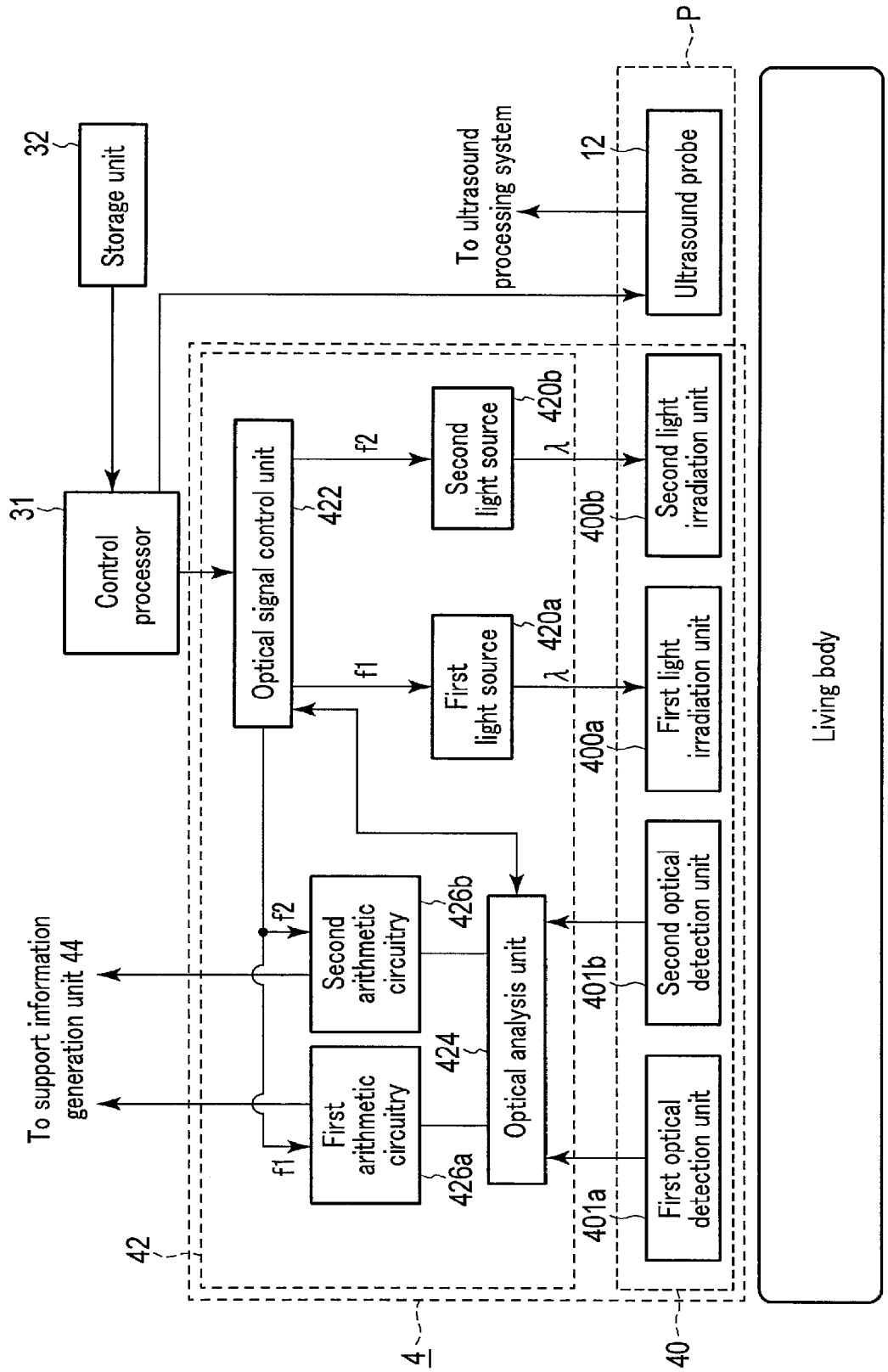
FIG. 4 is a block diagram for explaining the arrangement of an optical measurement processing unit 42.

According to one embodiment, an ultrasound diagnostic apparatus comprises an ultrasound probe, an optical probe, processing circuitry and an output unit. The ultrasound probe transmits an ultrasound wave from an ultrasound transmission/reception surface to an object and receives an ultrasound wave reflected by the inside of the object via the ultrasound transmission/reception surface. The optical probe includes a plurality of light sources configured to generate light beams respectively light-intensity modulated by different frequencies, a plurality of irradiation units respectively optically connected to the plurality of light sources and configured to irradiate the inside of the object with light beams generated by the respective light sources from a periphery of the ultrasound transmission/reception surface, and a plurality of optical detectors configured to detect intensities of light beams having the different peak wavelength which are applied from the respective irradiation units and diffused/reflected by the inside of the object, the optical probe being integrally provided with the ultrasound probe. The processing circuitry sets one of wavelengths of the plurality of light sources as a reference wavelength, normalizes an intensity of light having a wavelength other than the reference wavelength, which is detected by a pair of the each light irradiation unit and the each optical detector, with an intensity of light having the reference wavelength, calculates a first value for the each pair by nonlinear enhancement correction of the normalized light intensity, calculates a second value for the each pair by nonlinear reduction correction of an intensity of light having the reference wavelength detected by the each pair, and calculates an evaluation value based on a value obtained by multiplication of the first value and the second value for the each pair. The output unit outputs information for navigating a placement position of at least one the ultrasound probe and the optical probe to a suspected position based on the evaluation value.

An embodiment will be described below with reference to the accompanying drawing. Note that the same reference numerals in the following description denote constituent elements having almost the same functions and arrangements, and a repetitive description will be made only when required.

FIG. 1 is a block diagram showing the arrangement of an ultrasound diagnostic apparatus 1 according to this embodiment. The ultrasound diagnostic apparatus 1 shown in FIG. 1 includes a probe P, an input device 13, a monitor 14, an ultrasound transmission unit 21, an ultrasound reception unit 22, a B-mode processing unit 23, a blood flow detection unit 24, a RAW data memory 25, a volume data generation unit 26, an image processing unit 28, a display processing unit 30, a control processor (CPU) 31, a storage unit 32, an interface unit 33, an optical measurement processing unit 42, and a support information generation unit 44.

Note that the above constituent elements of the ultrasound diagnostic apparatus according to this embodiment can be broadly classified into the probe P including an ultrasound probe 12 and an optical probe 40, an optical measurement system which performs biomedical examination using light, and an ultrasound imaging system which obtains an image by ultrasound waves. These components will be separately described below.

(Probe P)

FIG. 2 is a view showing the probe P when viewed from the contact surface side with an object. FIG. 3 is a sectional view taken along A-A in FIG. 2 when viewed from the arrow direction. As shown in FIGS. 1 to 3, the probe P includes the ultrasound probe 12 and the optical probe 40.

The ultrasound probe 12 is a device (probe) which transmits ultrasound waves to an object, typically the living body, and receives reflected waves from the object based on the transmitted ultrasound waves. The ultrasound probe 12 has, on its distal end, an array of a plurality of piezoelectric transducers, a matching layer, a backing member, and the like. The piezoelectric transducers transmit ultrasound waves in a desired direction in a scan region based on driving signals from the ultrasound transmission unit 21, and convert reflected waves from the object into electrical signals. The matching layer is an intermediate layer which is provided for the piezoelectric transducers to make ultrasound energy efficiently propagate. The backing member prevents ultrasound waves from propagating backward from the piezoelectric transducers. When the ultrasound probe 12 transmits an ultrasound wave to the object, the transmitted ultrasound wave is sequentially reflected by a discontinuity surface of acoustic impedance of internal body tissue, and is received as an echo signal by the ultrasound probe 12. The amplitude of this echo signal depends on an acoustic impedance difference on the discontinuity surface by which the echo signal is reflected. The echo produced when a transmitted ultrasound pulse is reflected by a moving blood flow is subjected to a frequency shift depending on the velocity component of the moving body in the ultrasound transmission/reception direction by the Doppler effect.

Note that in this embodiment, the ultrasound probe 12 is a one-dimensional array probe having a plurality of ultrasound transducers arrayed along a predetermined direction. However, this is not exhaustive, and the ultrasound probe 12 may be a two-dimensional array probe (i.e., a probe having ultrasound transducers arranged in the form of a two-dimensional matrix) or a mechanical 4D probe (i.e., a probe which can execute ultrasound scanning while mechanically swinging an ultrasound transducer array in a direction perpendicular to the array direction), which can acquire volume data.

The optical probe 40 includes a plurality of light irradiation units 400 (two light irradiation units, namely, a first light irradiation unit 400a and a second light irradiation unit 400b, arranged near one of the short sides of the ultrasound transmission/reception surface of the ultrasound probe 12 in FIGS. 2 and 3), and a plurality of optical detection units 401 arranged symmetrically with respect to the longitudinal direction of the ultrasound transmission/reception surface along the longitudinal direction of the ultrasound transmission/reception surface of the ultrasound probe 12.

The first light irradiation unit 400a and the second light irradiation unit 400b respectively irradiate an object with light (near-infrared light) generated by a first light source 420a and a second light source 420b at different driving frequencies f1 and f2. In addition, the plurality of optical detection units 401 detect the intensities of light having specific wavelengths which are emitted from the first light irradiation unit 400a and the second light irradiation unit 400b and diffused/reflected by the inside of the object. Note that a slide mechanism may be provided, as needed, to move the plurality of optical detection units 401 relative to the first light irradiation unit 400a and the second light irradiation unit 400b.

(Ultrasound Imaging System)

The ultrasound transmission unit 21 includes trigger generation circuitry, delay circuitry, and pulse generation circuitry (none of which are shown). The trigger generation circuitry repetitively generates trigger pulses for the formation of transmission ultrasound waves at a predetermined rate frequency fr Hz (period: 1/fr sec). The delay circuitry gives each trigger pulse a delay time necessary to focus an ultrasound wave into a beam and determine transmission directivity for each channel. The pulse generation circuitry applies a driving pulse to the probe 12 at the timing based on this trigger pulse.

The ultrasound reception unit 22 includes amplifier circuitry, an A/D converter, delay circuitry, and an adder (none of which are shown). The amplifier circuitry amplifies an echo signal received via the probe 12 for each channel. The A/D converter converts each amplified analog echo signal into a digital echo signal. The delay circuitry gives the digitally converted echo signals delay times necessary to determine reception directivities and perform reception dynamic focusing. The adder then performs addition processing for the signals. With this addition, a reflection component from a direction corresponding to the reception directivity of the echo signal is enhanced to form a composite beam for ultrasound transmission/reception in accordance with reception directivity and transmission directivity.

The B-mode processing unit 23 receives an echo signal from the reception unit 22, and performs logarithmic amplification, envelope detection processing, and the like for the signal to generate data whose signal intensity is expressed by a luminance level.

The blood flow detection unit 24 extracts a blood flow signal from the echo signal received from the ultrasound reception unit 22, and generates blood flow data. In general, the blood flow detection unit 24 extracts a blood flow by CFM (Color Flow Mapping). In this case, the blood flow detection unit 24 analyzes the blood flow signal to obtain blood flow information such as mean velocities, variances, and powers as blood flow data at multiple points.

The raw data memory 25 generates B-mode raw data as B-mode data on three-dimensional ultrasound scanning lines by using a plurality of B-mode data received from the B-mode processing unit 23. The raw data memory 25 generates blood flow raw data as blood flow data on three-dimensional ultrasound scanning lines by using a plurality of blood flow data received from the blood flow detection unit 24. Note that for the purpose of reducing noise or smooth concatenation of images, a three-dimensional filter may be inserted after the raw data memory 25 to perform spatial smoothing.

The volume data generation unit 26 generates B-mode volume data or blood flow volume data by executing raw/voxel conversion including interpolation processing in consideration of spatial positional information.

The image processing unit 28 performs predetermined image processing such as volume rendering, MPR (Multi Planar Reconstruction), and MIP (Maximum Intensity Projection) for the volume data received from the volume data generation unit 26. Note that for the purpose of reducing noise or smooth concatenation of images, a two-dimensional filter may be inserted after the image processing unit 28 to perform spatial smoothing.

The display processing unit 30 executes various types of processing associated with a dynamic range, luminance (brightness), contrast, γ curve correction, RGB conversion, and the like for various types of image data generated/processed by the image processing unit 28.

The control processor 31 has the function of an information processing apparatus (computer) and controls the operation of each constituent element. The control processor 31 also executes processing in accordance with an ultrasound probe operation support function (to be described later).

The storage unit 32 stores a dedicated program for implementing a probe navigation function (to be described later) based on proximity evaluation values, obtained volume data, diagnosis information (patient ID, findings by doctors, and the like), a diagnostic protocol, transmission/reception conditions, and other data groups. The storage unit 32 is also used to store images in the image memory (not shown), as needed. It is possible to transfer data in the storage unit 32 to an external peripheral device via the interface unit 33. In addition, the storage unit 32 stores information concerning the moving distance of the probe P (to be described later), measurement data obtained by optical measurement, ultrasound probe operation support information, and ultrasound image data in association with each other for each measurement position.

The interface unit 33 is an interface associated with the input device 13, a network, and a new external storage device (not shown). In addition, an external biomedical examination apparatus can be connected to this ultrasound diagnostic apparatus main body 11 via the interface unit 33. The interface unit 33 can transfer data such as ultrasound images obtained by this apparatus, analysis results, and the like to other apparatuses via a network.

The support information generation unit 44 calculates at least one of the degree of adhesion between the ultrasound probe 12 and the surface of an object and the three-dimensional azimuth and distance (proximity) of an abnormal region in an object based on the three-dimensional position and distance of the abnormal region which are acquired at each measurement position upon movement of the probe P. The support information generation unit 44 then supports the operation of the ultrasound probe by generating and outputting support information for more favorably inducing the position, orientation, posture, pressure, and the like of the ultrasound probe 12 with respect to the object and the diagnostic target region based on the calculation result. The support information generation unit 44 also generates and outputs, based on determination results obtained by the optical measurement processing unit 42, information indicating insufficient pressurization, information indicating a re-measurement waiting state, and information indicating that an optical measurement error has occurred because a light intensity does not satisfy a predetermined condition. These pieces of information generated by the support information generation unit 44 are output (displayed) on, for example, the monitor 14 in a predetermined form. Note that as specific processing performed by the support information generation unit 44, for example, the technique disclosed in Jpn. Pat. Appl. KOKAI Publication No. 2014-110878 can be adopted, which is incorporated herein by reference.

(Optical Measurement System)

FIG. 4 is a block diagram for explaining the arrangement of the optical measurement processing unit 42. Assume that in this embodiment, a biomedical examination apparatus 4 is constituted by the optical probe 40, the optical measurement processing unit 42, a dedicated program which is stored in the storage unit 32 and is used to implement a probe navigation function based on proximity evaluation values, and the like. However, this is not exhaustive, and the biomedical examination apparatus 4 may include, for example, the support information generation unit 44 shown in FIG. 1, in addition to the optical probe 40 and the optical measurement processing unit 42. In addition, this embodiment exemplifies the biomedical examination apparatus 4 incorporated in the ultrasound diagnostic apparatus 1. However, this is not exhaustive, and the biomedical examination apparatus 4 may be separately formed to be detachable from the ultrasound diagnostic apparatus 1.

The first light source 420*a* and the second light source 420*b* are light-emitting elements such as semiconductor lasers, light-emitting diodes, solid-state lasers, or gas lasers which generate light having a wavelength exhibiting low biological absorption (e.g., light in the wavelength range of 600 nm to 1,800 nm, which is near the wavelength band called the biological window) and light having a specific wavelength exhibiting an increase in the amount of absorption of light in an abnormal region (e.g., light in the wavelength range of 750 nm to 850 nm, which falls within the wavelength band called the biological window and at which hemoglobin in blood absorbs light). An optical signal control unit 422 supplies different driving frequencies (f1 and f2 in this case) to the first light irradiation unit 400*a* and the second light irradiation unit 400*b*. Light beams generated by the first light source 420*a* and the second light source 420*b* are respectively supplied to the first light irradiation unit 400*a* and the second light irradiation unit 400*b* via, for example, an optical waveguide formed from an optical fiber or thin-film optical waveguide. As a result, the first light irradiation unit 400*a* and the second light irradiation unit 400*b* emit light beams having specific wavelengths at the different driving frequencies. Assume that in this embodiment, the peak wavelength of the first light source 420*a* is different from the peak wavelength of the second light source 420*b*.

The plurality of optical detection units 401 are formed from a plurality of detection elements which have detection surfaces formed from, for example, end portions of optical fibers, and photoelectrically convert reflected light beams from the inside of the object which are input from the detection surfaces via optical waveguide portions. As each detection element, for example, a CCD, APD, photomultiplier tube, or the like can be adopted, as well as a light-receiving element such as a photodiode or phototransistor. The contact surfaces of each light irradiation unit 400 and each optical detection unit 401 with respect to the object may be provided with optical matching layers.

The optical signal control unit 422 dynamically or statically controls the biomedical examination apparatus 4. For example, the optical signal control unit 422 controls the first light source 420*a* and the second light source 420*b* (the first light source 420*a* and the second light source 420*b* have different driving frequencies in this embodiment, in particular) under the control of the control processor 31 of the ultrasound diagnostic apparatus 1 so as to make the first light irradiation unit 400*a* and the second light irradiation unit 400*b* emit light at predetermined timings, predetermined frequencies, intensities, and intensity variation periods. In addition, the optical signal control unit 422 controls an optical analysis unit 424 so as to execute analysis processing corresponding to light with a predetermined driving period at a predetermined timing.

The optical analysis unit 424 includes a multi-channel lock-in amplifier. The optical analysis unit 424 selects frequencies f1 and f2, detects only predetermined signals, and amplifies them. The optical analysis unit 424 then converts the signals into digital signals. The optical analysis unit 424 also analyzes a change in the intensity of detected light between the optical detection units 401. This analysis is executed for each measurement data acquired at each measurement position.

The optical analysis unit 424 includes a processor (processing circuitry) and a memory. The optical analysis unit 424 calculates light intensities normalized by using light intensities corresponding to the respective wavelengths which are sequentially measured and a light intensity as a geometrical means, and analyzes temporal changes in them. The optical analysis unit 424 also determines, based on an analysis result on the temporal changes in light intensities, whether the pressure of the probe P on an object PS is proper and a measured light intensity satisfies a condition suitable for the calculation of an oxygen saturation ratio or the like. In addition, the optical analysis unit 424 implements a probe navigation function based on proximity evaluation values.

In response to a determination result, as a trigger, obtained by the optical analysis unit 424, which indicates that a measured light intensity satisfies a predetermined condition, based on a change in the intensity of detected light between the optical detection units 401, which is obtained at each measurement position, first arithmetic circuitry 426*a* calculates the three-dimensional position and distance of an abnormal region indicating a predetermined light absorption coefficient in the object (e.g., a region which absorbs light with a specific wavelength more than a normal tissue) with reference to the degrees of adhesion between the plurality of optical detection units 401 and the surface of the object, the depth of the abnormal region from the surface of the object, and a predetermined position (e.g., the light irradiation unit 400, the ultrasound transmission/reception surface center of the ultrasound probe 12, or the like). The calculation results obtained by the first arithmetic circuitry 426*a* are sent to the support information generation unit 44 for each measurement position. Note that the arrangement and function of second arithmetic circuitry 426*b* are substantially the same as those of the first arithmetic circuitry 426*a*.

(Example of Circuit Diagram of Optical Measurement System)

Figure 5:
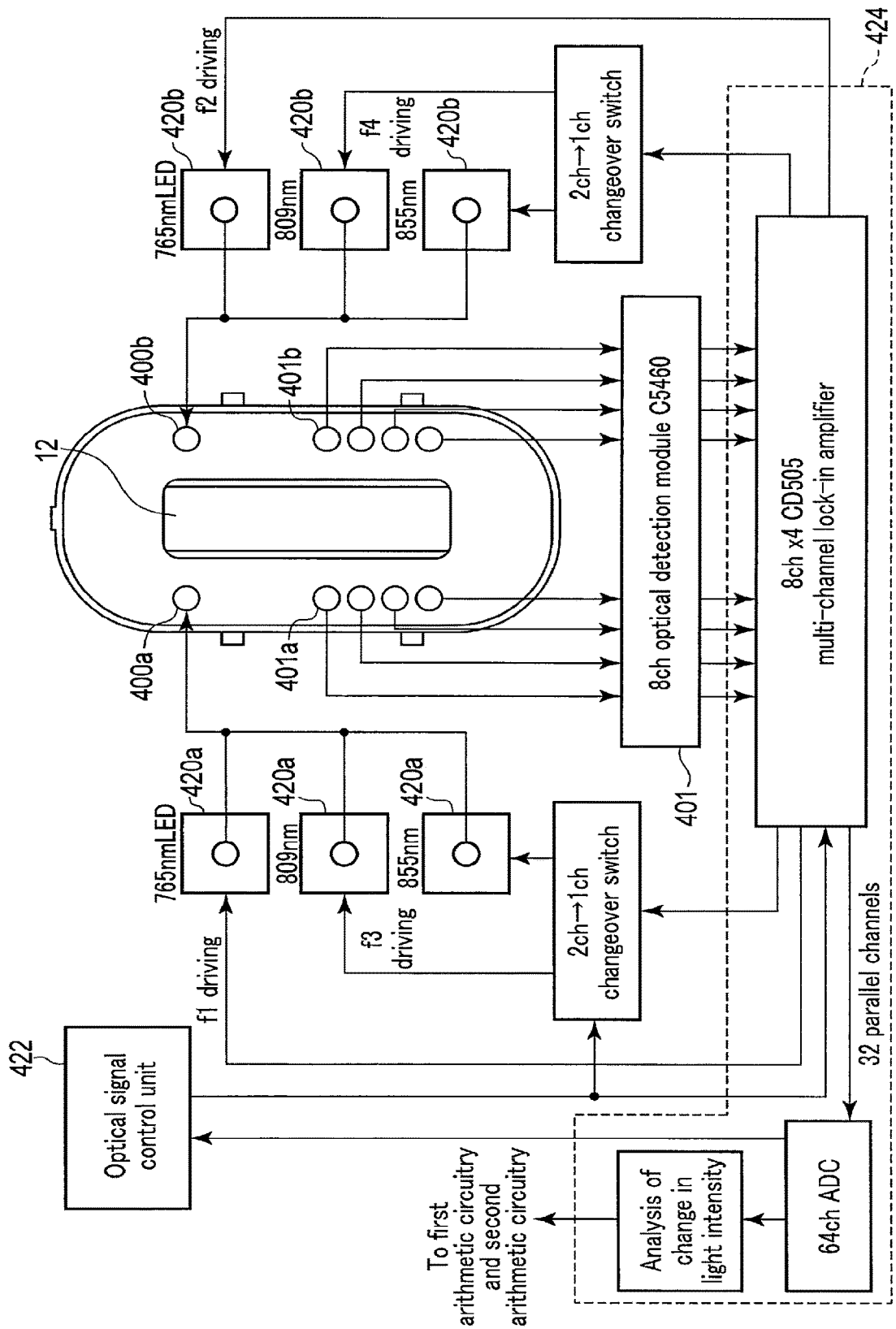
FIG. 5 is a view showing the circuit arrangement of the optical measurement system of a biomedical examination apparatus 4.

FIG. 5 is a view showing an example of the circuit arrangement of the optical measurement system of the biomedical examination apparatus 4. In the case shown in FIG. 5, optical measurement using three different wavelengths is implemented. For the first light irradiation unit 400*a*, three light sources 420*a*1, 420*a*2, and 420*a*3 (LEDs) with peak wavelengths $\lambda 1$, $\lambda 2$, and $\lambda 3$ ($\lambda 1$=765 nm, $\lambda 2$=809 nm, and $\lambda 3$=855 nm in the case shown in FIG. 5) are used. Likewise, for the second light irradiation unit 400*b*, three light sources 420*b*1, 420*b*2, and 420*b*3 (LEDs) with peak wavelengths $\lambda 1$, $\lambda 2$, and $\lambda 3$ are used. The light source 420*a*1 is driven at a frequency f1. The light sources 420*a*2 and 420*a*3 are driven at a frequency f3. The light source 420*b*1 is driven at a frequency f2. The light sources 420*b*2 and 420*b*3 are driven at a frequency f4.

As the driving frequencies (f1, f2, f3, and f4), phase detection reference signals supplied from a multi-channel lock-in amplifier (to be described later) are used. Light beams generated by the respective light sources are respectively transferred toward the first light irradiation unit 400*a* and the second light irradiation unit 400*b* through optical fibers.

The first light irradiation unit 400*a* and the second light irradiation unit 400*b* irradiate the living body with light. Light from the living body enters each of the optical detection units 401 (eight optical detection units in the case shown in FIG. 5) and is transferred to an 8 ch optical detection module constituted by photoelectric conversion elements (a photodiode, avalanche photodiode, phototransistor, and the like) via an optical fiber. Note that using a device having a multiplying effect such as an avalanche photodiode as a photoelectric conversion element can improve the SN ratio. Amplification circuitry converts each of photocurrents with the driving frequencies f1, f2, f3, and f4 into a photocurrent having a proper potential and circuit impedance. Each photocurrent is then input to a multichannel lock-in amplifier (in the case shown in FIG. 5, a parallel 8 ch optical detection module is connected to a parallel 8×4 (32) ch lock-in amplifier to perform detection with four frequencies). A 64 ch A/D converters photocurrents concurrently output from the 32 ch multi-channel lock-in amplifier. The optical analysis unit 424 analyzes a change in intensity between the optical detection units 401 and a temporal change in light intensity in each optical detection unit 401. These processes are executed for an optical signal acquired at each measurement position along with the movement of the probe P.

(Input Device/Monitor)

The input device 13 is connected to an apparatus main system 11 and includes various types of switches which are used to input, to the apparatus main body 11, various types of instructions, conditions, an instruction to set a region of interest (ROI), various types of image quality condition setting instructions, and the like from an operator, a switch for switching between a rough search mode and a fine adjustment mode which will be described later, buttons, a trackball, a mouse, and a keyboard. In addition, the input device 13 includes a button or the like for instructing the timing to capture paracentesis information including the position of the tip of a puncture needle in a paracentesis support function (to be described later).

The monitor 14 displays morphological information and blood flow information in the living body as images based on video signals from the display processing unit 30.

(Optical Biomedical Measurement Accompanied with Movement of Probe P)

The biomedical examination apparatus 4 according to this embodiment executes optical biomedical measurement at a plurality of measurement positions (i.e., a series of operations including irradiating the inside of the living body with light by the plurality of light irradiation units 400 and optical detection from the inside of the living body by the plurality of optical detection units 401) while manually moving the probe P.

Note that any technique can be used for optical measurement at each measurement position. This embodiment will exemplify a case in which optical measurement is performed at a plurality of measurement positions in accordance with the rough search mode and the fine adjustment mode, while the probe P is moved, and, for example, the depth of an abnormal region from the surface of the object is calculated by using measurement data at each measurement position. In this case, the rough search mode is a mode for roughly searching for an abnormal region when adjusting the position of the probe P on the surface of the living body so as to make the ultrasound scan slice of the ultrasound probe 12 include a diagnostic target region (a region recognized as the abnormal region or suspected to have abnormality) in the living body. The fine adjustment mode is a mode for accurately searching for the abnormal region when adjusting the position of the ultrasound probe 12 on the surface of the living body.

FIG. 6A is a view for explaining optical measurement processing complying with the rough search mode. As shown in FIG. 6A, in the rough search mode, the first light irradiation unit 400a is paired with a plurality of optical detection units 401a, and the second light irradiation unit 400b is paired with a plurality of optical detection units 401b (that is, the light irradiation unit and the detection units arranged on the same side of the ultrasound probe 12 are paired).

After the pairing, optical biomedical measurement is executed at a plurality of measurement positions, the position of the probe P is changed while the probe P is repeatedly pressed on and relaxed from the object, by using a region (first search range) searched by the first light irradiation unit 400a and the plurality of optical detection units 401a and a region (second search range) searched by the second light irradiation unit 400b and the plurality of optical detection units 401h. At this time, for example, if a light signal displacement in a specific frequency band corresponding to a diagnostic target region which is detected from the second search range is larger in intensity than that from the first search range, it indicates that the diagnostic region exists closer to the second search range than the center (long axis) of the ultrasound probe 12. On the contrary, if such a signal detected from the first search range is higher in intensity than that from the second search range, it indicates that the diagnostic region exists closer to the first search range than the center (long axis) of the ultrasound probe 12. In the rough search mode, relatively large regions for searching for an abnormal region can be set on the two sides of the ultrasound irradiation surface of the ultrasound probe 12. It can be said from these characteristics that this mode is suitable to guide a diagnostic target region near the ultrasound probe.

In contrast, the fine adjustment mode is executed after, for example, rough position adjustment is performed through the rough detection mode. FIG. GB is a view for explaining optical measurement processing complying with the fine adjustment mode. As shown in FIG. 6B, in the fine adjustment mode, the first light irradiation unit 400a is paired with the plurality of optical detection units 401b, and the second light irradiation unit 400b is paired with the plurality of optical detection units 401a (that is, the light irradiation units and the detection units arranged on the two sides of the ultrasound probe 12 are respectively paired).

After the pairing, optical biomedical measurement is executed at a plurality of measurement positions, while the position of the probe P is changed, by using a region (first search range) searched by the first light irradiation unit 400a and the plurality of optical detection units 401b and a region (second search range) searched by the second light irradiation unit 400b and the plurality of optical detection units 401a. At this time, for example, it is possible to narrow down the position of a diagnostic target region near the center of the probe P by comparing the displacement of a light intensity signal in a specific frequency band corresponding to the diagnostic target region which is detected from the first search range with that detected from the second search region. In the fine adjustment mode, an area for searching for an abnormal region is set so as to include the ultrasound irradiation surface of the ultrasound probe 12. It can be said from these characteristics that this mode is suitable to accurately guide a diagnostic target region into the ultrasound scanning surface.

Note that the rough search mode and the fine adjustment mode are switched from each other by, for example, an operation with the input device 13. However, this is not exhaustive. For example, the apparatus may automatically select the rough search mode or the fine adjustment mode by comparing the distance between a diagnostic target region and the ultrasound transmission/reception surface with a predetermined threshold.

(Probe Navigation Function Based on Proximity Evaluation Values)

A technological background based on experimental facts will be described first. FIG. 7A is a graph showing the spatial distribution of normalized light intensity ratios of light with a wavelength of 855 nm to light with a wavelength of 765 nm with respect to a simulated benign tumor and a simulated malignant tumor, with the abscissa representing the distances of light source positions with reference to an end face of a phantom. In addition, FIG. 7B is a graph showing light intensities with wavelengths of 855 nm and 765 nm (or values obtained by normalizing the light intensities with initial values (reference values)) detected at predetermined positions with respect to a simulated benign tumor and a simulated malignant tumor.

As is obvious from FIG. 7A, it is possible to reduce the influences of composition variations and changes and fluctuations of measured values on normalized light intensity ratios. On the other hand, it is sometimes impossible to present a normalized light intensity ratio sufficient for discrimination between a benign tumor and a malignant tumor. In addition, as is obvious from FIG. 7B, the light intensities with wavelengths of 855 nm and 765 nm themselves notably represent differences between a benign tumor and a malignant tumor. In contrast, with regard to the accuracy of light intensities, their SN ratios are greatly influenced by composition variations and changes and fluctuations of measured values. It is therefore required to perform signal processing utilizing the advantages of normalized light intensities and detected light intensity ratios themselves.

Under this circumstance, the ultrasound diagnostic apparatus or biomedical examination apparatus according to this embodiment sets one of a plurality of wavelengths as a reference wavelength, and normalizes, with the intensity of light having the reference wavelength, the intensity of light having a wavelength, other than the reference wavelength, which is detected by a pair of each light irradiation unit and each optical detection unit, and calculates a first value for each pair by nonlinear enhancement correction of the normalized light intensity. In addition, the apparatus calculates a second value for each pair by nonlinear reduction correction of the intensity of light having the reference wavelength detected by each pair, and calculates a proximity evaluation value based on a value obtained by multiplication of the first value and the second value for each pair. This proximity evaluation value is not greatly influenced by variations in measured value, and hence can be used as a parameter notably representing the difference between a region without any abnormality and a malignant tumor (or suspected region).

As described above, in optical measurement processing, after the placement position (imaging position) of the probe P including the optical probe 40 is roughly searched out first in accordance with the rough search mode, optical measurement used for fine adjustment of the placement position of the probe P and quantification of an oxygen saturation is performed in the fine adjustment mode. The ultrasound diagnostic apparatus 1 according to this embodiment calculates a proximity evaluation value in real time in the rough search mode, and outputs navigation information for notifying the operator how much the probe P approaches an abnormal region as a target in a predetermined form in real time based on the proximity evaluation value sequentially obtained as a result of the calculation.

Figure 8:
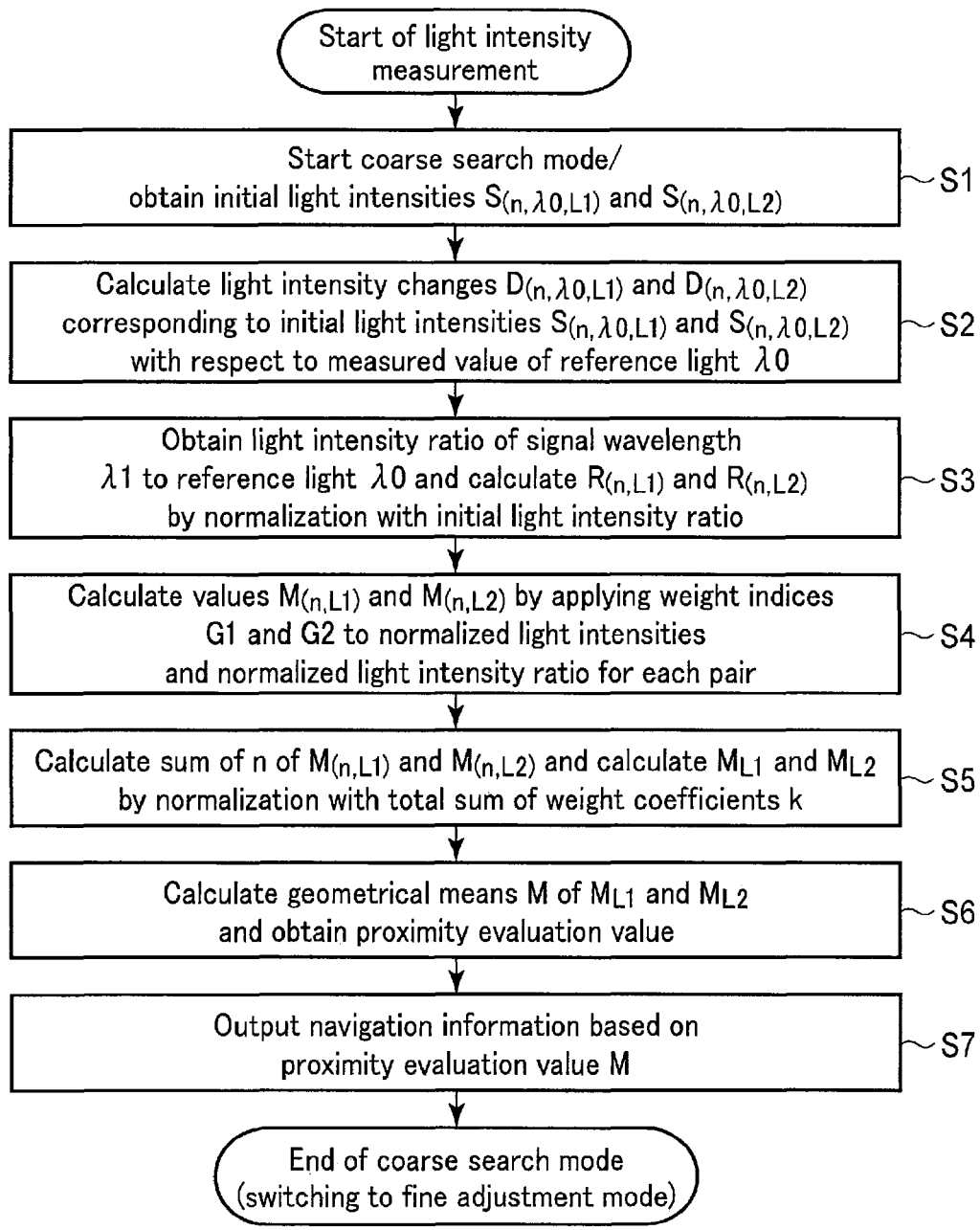
FIG. 8 is a flowchart showing probe navigation processing based on proximity evaluation values, which is executed in the rough search mode.

FIG. 8 is a flowchart showing processing complying with the probe navigation function based on proximity evaluation values (probe navigation processing based on proximity evaluation values), which is executed in the rough search mode. The concrete contents of the probe navigation processing based on proximity evaluation values will be described with reference to FIG. 8.

For the sake of concreteness, assume that two types of light beams having different wavelengths ($\lambda 0$=809 nm, $\lambda 1$=765 nm) are used to measure deoxygenated hemoglobin and oxygenated hemoglobin, and a proximity evaluation value is calculated by using $\lambda 0$=809 nm as a reference wavelength. However, this is not exhaustive. For example, another light having a wavelength of 855 nm or the like can be used instead of light having a wavelength of 809 nm for measuring oxygenated hemoglobin. In addition, $\lambda 1$=765 nm can be used as a reference wavelength. Furthermore, for the sake of illustrative convenience, assume that the first light irradiation unit 400a and the second light irradiation unit 400b are respectively written as L1 and L2, and four first optical units 401a1 to 401a4 and four second optical detection units 401b1 to 401b4 are symbolically written as a first optical detection unit 401an and a second optical detection unit 401bn (where n=1, 2, 3, and 4), respectively, in FIG. 8.

As shown in FIG. 8, when light intensity measurement is started, the rough search mode is started (step S0). The optical signal control unit 422 causes the first light irradiation unit 400a and the second light irradiation unit 400b to irradiate an object with light beams having two wavelengths ($\lambda 0$=809 nm and $\lambda 1$=765 nm in this case) at predetermined periods while the probe P is lightly touching the object surface. The first optical detection unit 401an and the second optical detection unit 401bn respectively detect light beams emerging from the object due to the applied light beams. The optical analysis unit 424 obtains initial light intensities (reference intensities) $s_{(n,\lambda 0,L1)}$, $s_{(n,\lambda 1,L1)}$, $s_{(n,\lambda 0,L2)}$ and $s_{(n,\lambda 1,L2)}$ concerning L1 and L2 by using the two-wavelength light intensity data detected by the first optical detection unit 401an and the second optical detection unit 401bn (step S1).

Subsequently, after a lapse of a predetermined period, the optical analysis unit 424 calculates light intensity changes in initial light intensities $s_{(n,\lambda 0,L1)}$ and $s_{(n,\lambda 0,L2)}$, in terms of reciprocals, with respect to light intensities $i_{(n,\lambda 0,L1)}$ and $i_{(n,\lambda 0,L2)}$ of a reference wavelength $\lambda 0$ respectively detected by the first optical detection unit 401an and the second optical detection unit 401bn according to equations (11) and (12) (step S2).

$$D_{(n,\lambda 0,L1)} = s_{(n,\lambda 0,L1)} / i_{(n,\lambda 0,L1)} \quad (11)$$

$$D_{(n,\lambda 0,L2)} = s_{(n,\lambda 0,L2)} / i_{(n,\lambda 0,L2)} \quad (12)$$

The optical analysis unit 424 then obtains the light intensity ratio of the measured value of the wavelength $\lambda 1$ to the measured value of the reference wavelength $\lambda 0$, and calculates values $R_{(n,L1)}$ and $R_{(n,L2)}$ normalized with the light intensity ratio between the initial values according to equations (21) and (22) (step S3).

$$R_{(n,L1)} = \{i_{(n,\lambda 0,L1)}/i_{(n,\lambda 1,L1)}\}/\{s_{(n,\lambda 0,L1)}/s_{(n,\lambda 1,L1)}\} \quad (21)$$

$$R_{(n,L2)} = \{i_{(n,\lambda 0,L2)}/i_{(n,\lambda 1,L2)}\}/\{s_{(n,\lambda 0,L2)}/s_{(n,\lambda 1,L2)}\} \quad (22)$$

The optical analysis unit 424 calculates values $M_{(n,L1)}$ and $M_{(n,L2)}$ obtained by applying weights to the normalized light intensity and the normalized intensity ratio for each of pairs of the first light irradiation unit 400a (L1) and the first optical detection unit 401an and the second light irradiation unit 400b (L2) and the second optical detection unit 401bn according to equations (41) and (42) (step S4).

$$M_{(n,L1)} = K_{(n,L1)} \cdot D_{(n,L1)}^{G1} \cdot R_{(n,L1)}^{G2} \quad (41)$$

$$M_{(n,L2)} = K_{(n,L2)} \cdot D_{(n,L2)}^{G1} \cdot R_{(n,L2)}^{G2} \quad (42)$$

where $K_{(n,L1)}$ and $K_{(n,L2)}$ are weight coefficients set in correspondence with the pairs of the first light irradiation unit 400a (L1) and the first optical detection unit 401an and the second light irradiation unit 400b (L2) and the second optical detection unit 401bn, and $G_1$ and $G_2$ are weight indices respectively set for a normalized reference light intensity and a normalized light intensity ratio. Note that $K_{(n,L1)}$, $K_{(n,L2)}$, $G_1$, and $G_2$ are set to preferable values by external setting. The preferable values of $G_1$ and $G_2$ in breast cancer examination will be described in detail later. The equations (41) and (42) perform exponential correction as the nonlinear enhancement correction and the nonlinear reduction correction.

The optical analysis unit 424 then calculates the sum of n of $M_{(n,L1)}$ and $M_{(n,L2)}$ respectively corresponding to L1 and L2 according to equations (51) and (52). The optical analysis unit 424 obtains $M_{L1}$ and $M_{L2}$ respectively corresponding to L1 and L2 by normalizing the obtained values with the total sum of the weight coefficients $K_{(n,L1)}$ and $K_{(n,L2)}$ (step S5).

$$M_{L1} = \Sigma_{n=1-4} M_{(n,L1)} / \Sigma_{n=1-4} K_{(n,L1)} \quad (51)$$

$$M_{L2} = \Sigma_{n=1-4} M_{(n,L2)} / \Sigma_{n=1-4} K_{(n,L2)} \quad (52)$$

The optical analysis unit 424 then obtains a proximity evaluation value M by calculating the geometrical mean of $M_{L1}$ and $M_{L2}$ with respect to the two light irradiation units L1 and L2 according to equation (61) (step S6).

$$M = (M_{L1} \cdot M_{L2})^{1/2}$$

Each process in steps S2 to S6 is sequentially repeatedly executed in real time. The control processor 31 outputs, in real time, sequentially in accordance with the value of M, navigation information for notifying the operator how much the probe P has approached an abnormal region as a target in a predetermined form (for example, notifying the approach of the probe to the abnormal region with different musical notes or displaying, on the monitor 14, an object for notifying the approach of the probe to the abnormal region). In ultrasound diagnosis, in particular, the operator needs to alternately observe the patient and the monitor 14 while operating the probe P. Therefore, to output navigation information in the form of sound is suitable as an example of allowing the operator to easily grasp the approach of the probe without imposing much load on the operator.

Although FIG. 8 exemplarily shows the data processing in the rough search mode, similar processing can be performed in the fine adjustment and other modes as well.

Figure 9:
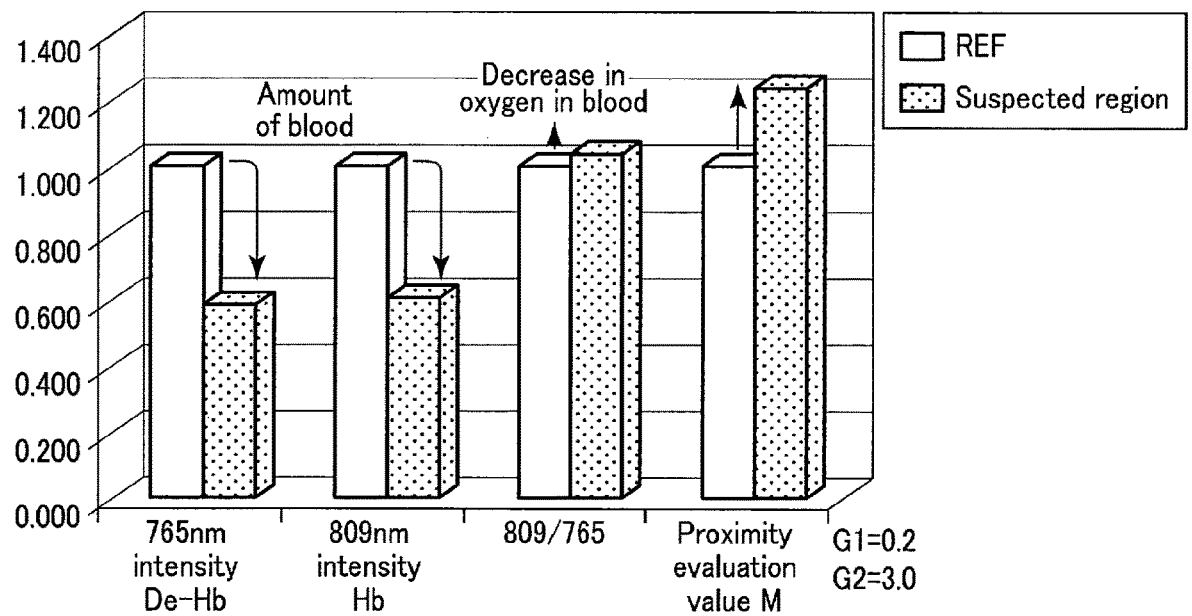
FIG. 9 is a graph showing measured light intensities, a normalized value, and a proximity evaluation value together with corresponding reference values.

FIG. 9 is a graph showing values obtained by normalizing light intensities measured using light beams having peak wavelength λ0=809 nm and peak wavelength λ1=765 nm on the body surface of a region suspected as abnormal on the body surface of a suspected region with initial light intensities (reference values measured in a healthy region), a value obtained by normalizing the intensity of light having a peak wavelength of 809 nm with the intensity of light having a peak wavelength of 765 nm, and a proximity evaluation value obtained by processing complying with FIG. 8, together with the corresponding reference values. Note that in the proximity evaluation value calculation shown in FIG. 9, the values of the weight indices G1 and G2 were respectively set to 0.2 and 3.0.

As shown in FIG. 9, since the intensity of light having a wavelength of 809 m greatly decreases as compared with the reference value, it is known that the amount of oxygen in blood (oxygenated hemoglobin) is reduced, and hence it is estimated that a region suspected as abnormal exists immediately below the body surface. However, the value obtained by normalizing the intensity of light having a wavelength of 809 nm with the intensity of light having a wavelength of 765 nm exhibits only a small difference from the reference value. That is, the value is not a parameter satisfactorily showing a reduction in the amount of oxygen in blood. In contrast to this, the proximity evaluation value obtained by the processing complying with FIG. 8 indicates a notable difference from the reference value, and hence is a parameter satisfactorily showing a reduction in the amount of oxygen in blood. The control processor 31 outputs, as navigation information, a sound corresponding to a clear different indicated by a proximity evaluation value in this manner (for example, a sound increasing in pitch in accordance with a difference from an proximity evaluation value). The operator can intuitively grasp the approach of the probe P to the body surface of a region suspected as abnormal.

Figure 10:
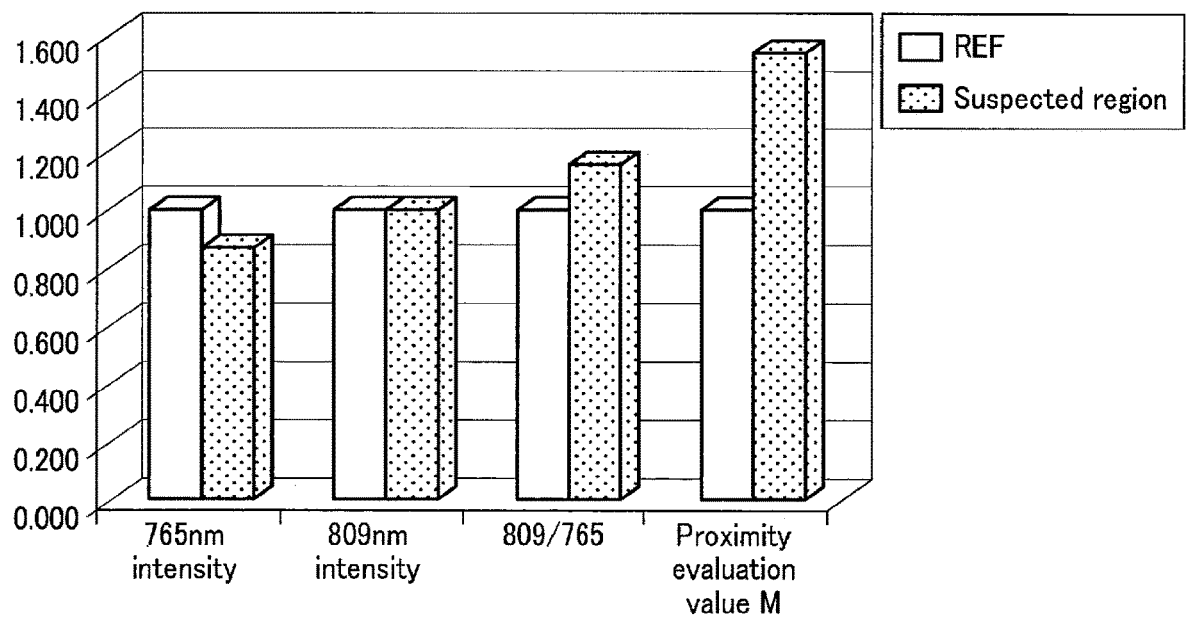
FIG. 10 is a graph similar to that shown in FIG. 9 with respect to a patient different from the one in FIG. 9.
Figure 21:
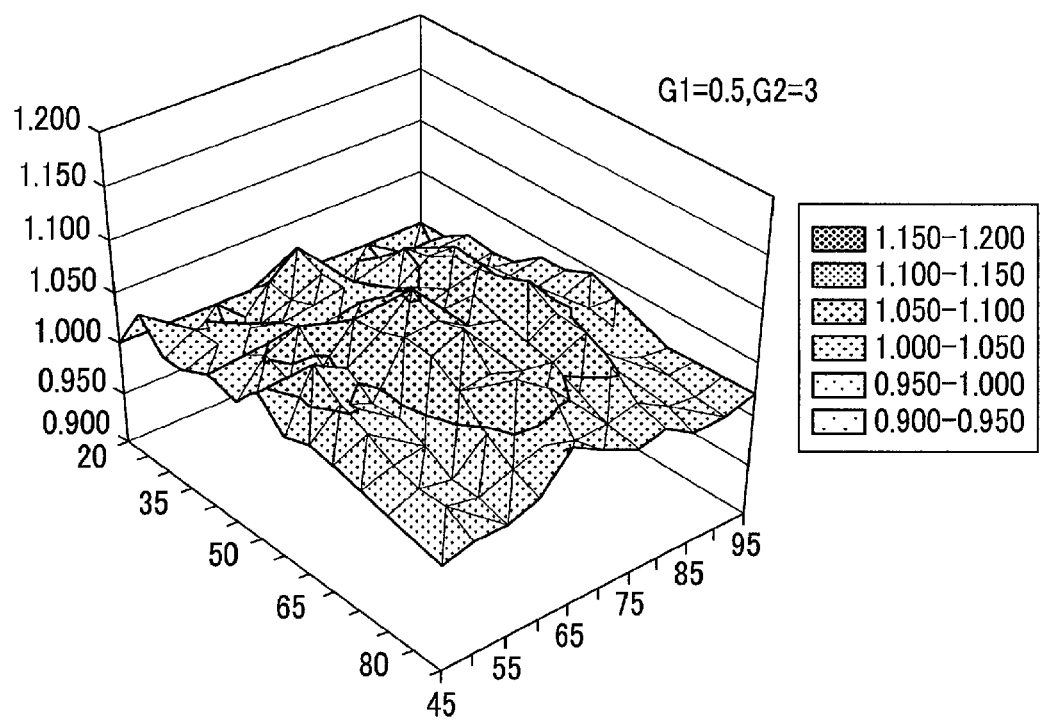
FIG. 21 is a graph showing the distribution of proximity evaluation values when the weight indices G1 and G2 are set to (0.5, 3)
Figure 22:
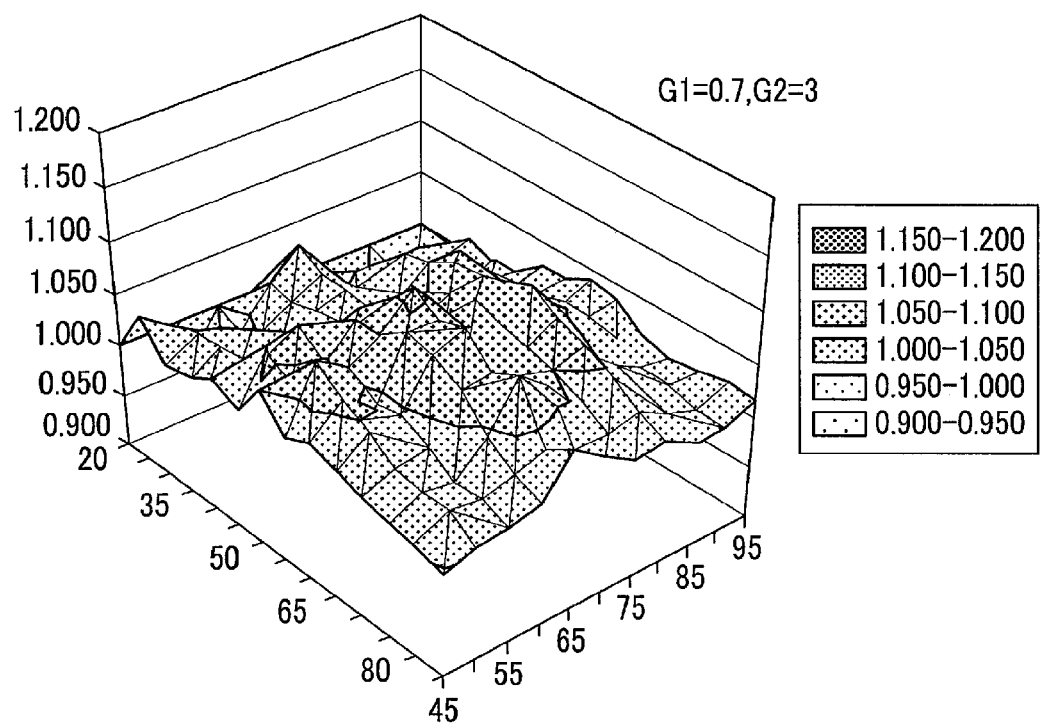
FIG. 22 is a graph showing the distribution of proximity evaluation values when the weight indices G1 and G2 are set to (0.7, 3)

FIG. 10 is a graph similar to that shown in FIG. 9 with respect to a patient different from the one in FIG. 9. As is obvious from FIG. 10, the patient exhibits small changes in both the intensity of light having a wavelength of 765 nm and the intensity of light having a wavelength of 809 nm with respect to the reference values. For this reason, it looks as if the probe P did not approach the region suspected as abnormal. However, the value obtained by normalizing the intensity of light having a wavelength of 809 nm with the intensity of light having a wavelength of 765 nm shows a clear difference from the reference value. In addition, the proximity evaluation value obtained by the processing complying with FIG. 8 shows a more notable difference from the reference value. The control processor 31 outputs, for example, a sound corresponding to such a clear difference indicated by a proximity evaluation value as navigation information. Using the navigation information will reduce the chance that the operator will overlook the approach of the probe P to a region suspected as abnormal as compared with using a light intensity itself.

FIG. 11 is a graph showing the spatial distribution of values obtained by normalizing light intensities measured using light having wavelength λ1=765 nm with an initial value at the time of optical measurement of a phantom in which a simulated tumor (a depth of 20 mm and a diameter of 10 mm) is embedded, with respect to the central axis position of the probe P and the light source position. FIGS. 12, 13, and 14 are graphs similar to the distribution in FIG. 11, respectively showing the distributions of values obtained by normalizing light intensities measured by using light having wavelength λ0=809 nm with an initial value, values obtained by normalizing the intensities of light having a wavelength of 809 nm with the intensities of light having a wavelength of 765 nm, and proximity evaluation values obtained by the processing complying with FIG. 8. It is obvious from FIGS. 11 to 14 that using the proximity evaluation values make differences from the healthy region more notable, which have not been clear with the values obtained by normalizing the intensities of light having a wavelength of 809 nm with the intensities of light having a wavelength of 765 nm.

(Weight Indices)

The weight indices G1 and G2 can be set to desired values by, for example, manual operations or selection of values from a plurality of recommended values. However, the values of the weight indices G1 and G2 are preferably set in accordance with a diagnosis target, as needed. The suitable values of the weight indices G1 and G2 will be described below by exemplifying a medical examination for breast cancer using an ultrasound diagnostic apparatus.

FIGS. 15, 16, 17, and 18 are graphs showing the distributions of proximity evaluation values corresponding to the central axis position of the probe P and the light source position when weight indices G1 and G2 are set to (0.1, 1), (0.1, 2), (0.1, 3), and (0.1, 5) at the time of optical measurement of the same phantom as that shown in FIG. 11. Comparing FIGS. 15 to 18 with each other makes it possible to determine the influences of changes in G2 on the distributions of proximity evaluation values while G1 is fixed. For example, it is obvious from the comparisons between these distributions that, for example, $1 < G2 \leq 4$ is suitable to breast cancer examination using the ultrasound diagnostic apparatus.

FIGS. 19, 20, 21, 22, 23, and 24 are graphs respectively showing the distributions of proximity evaluation values at the time of optical measurement of the same phantom as that shown in FIG. 11 with respect to the central axis position of the probe P and the light source position when the weight indices G1 and G2 are set to (0.1, 3), (0.3, 3), (0.5, 3), (0.7, 3), (1, 3), and (2, 3). Comparing FIGS. 19 to 24 with each other makes it possible to determine the influences of changes in G1 on the distributions of proximity evaluation values while G2 is fixed. It is obvious from the comparisons between these distributions that, for example, $0 < G1 \leq 1$ is suitable to breast cancer examination using the ultrasound diagnostic apparatus.

The ultrasound diagnostic apparatus or biomedical examination apparatus according to the embodiment described above sets one of a plurality of wavelengths as a reference wavelength, normalizes the intensity of light having a wavelength other than the reference wavelength, which is detected by a pair of each light irradiation unit and each optical detection unit, with the intensity of light having the reference wavelength, and performs nonlinear enhancement correction of the normalized light intensity, thereby calculating a first value for each pair. In addition, the apparatus calculates a second value for each pair by performing nonlinear reduction correction of the intensity of light having the reference wavelength detected by each pair, and calculates a proximity evaluation value based on a value obtained by multiplication of the first value and the second value for each pair. This proximity evaluation value indicates the enhanced difference between a healthy region and a suspected region more than that indicated by a measurement result obtained by using a light intensity detected by each optical detector without any change. When, therefore, the probe is guided to near a suspected region, it is possible to provide more easily comprehensive navigation information for the operator. This makes it possible to easily and quickly guide the probe to a desired position. It is therefore possible to provide an ultrasound diagnostic apparatus which is more user-friendly than the related art.

The above described "processor" or "processing circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasound diagnostic apparatus comprising: an ultrasound probe configured to transmit an ultrasound wave from an ultrasound transmission and a reception surface to an object and receive the ultrasound wave that has propagated through the object via the ultrasound transmission and the reception surface;
   an optical probe including a plurality of light sources of different peak wavelengths configured to generate light beams respectively light-intensity modulated by different frequencies, and a plurality of optical detectors configured to detect intensities of light beams having the different peak wavelengths which are radiated from the respective light sources and propagated through an inside of the object, the optical probe being integrally provided with the ultrasound probe; and
   processing circuitry configured to set a first intensity of a first light beam with a reference wavelength detected by one of the plurality of optical detectors, the reference wavelength being selected from one of the different peak wavelengths of the plurality of light sources, normalize second intensities of second light beams detected by the plurality of optical detectors with the first intensity of the first light beam having the reference wavelength, the second light beams being different from the first light beam with the reference wavelength, calculate a first value by nonlinear enhancement correction of the normalized second intensities of the second light beams, calculate a second value by nonlinear reduction correction of the first intensity of the first light beam having the reference wavelength, calculate an evaluation value based on the first value and the second value, and
   output information for navigating a placement position of at least one of the ultrasound probe and the optical probe to a suspected position based on the evaluation value.

2. The ultrasound diagnostic apparatus of claim 1, wherein the processing circuitry calculates the evaluation value by multiplying the first value and the second value for each of the second intensities detected by the plurality of optical detectors.

3. The ultrasound diagnostic apparatus of claim 1, wherein the processing circuitry is configured to perform the nonlinear enhancement correction and the nonlinear reduction correction according to a following equation:
$$M_{(n, Lm)} = K_{(n, Lm)} \cdot D_{(n, Lm)}^{G1} \cdot R_{(n, Lm)}^{G2}$$
where n is a first number of the plurality of the optical detectors, Lm is a second number of the plurality of the light sources, $M_{(n, Lm)}$ is a proximity evaluation value, $K_{(n, Lm)}$ is a weight coefficient, $G_1$ is a first power index for a normalized reference light intensity in terms of reciprocal $D_{(n, Lm)}$ and $G_2$ is a second power index for a normalized light intensity ratio $R_{(n, Lm)}$.

4. The ultrasound diagnostic apparatus of claim 3, wherein the processing circuitry sets the first power index $G_1$ to $0 < G_1 \leq 1$, and sets the second power index $G_2$ to $1 < G_2 \leq 4$.

5. The ultrasound diagnostic apparatus of claim 3, wherein the processing circuitry is configured to calculate the proximity evaluation value by applying weights to normalized light intensities and ratios.

6. The ultrasound diagnostic apparatus of claim 1, wherein the evaluation value is a first evaluation value, the processing circuitry is configured to normalize a second evaluation value of a suspected region with a third evaluation value of a healthy region.

7. A biomedical examination apparatus comprising:
   an optical probe including a plurality of light sources of different peak wavelengths configured to generate light beams respectively light-intensity modulated by different frequencies, and a plurality of optical detectors configured to detect intensities of light beams having the different peak wavelengths which are applied from the respective light sources, propagated through an inside of an object, and integrally provided with an ultrasound probe; and
   processing circuitry configured to set a first intensity of a first light beam with a reference wavelength detected by one of the plurality of optical detectors, the reference wavelength being selected from one of the different peak wavelengths of the plurality of light sources, normalize second intensities of second light beams detected by the plurality of optical detectors with the first intensity of the first light beam having the reference wavelength, the second light beams being different from the first light beam with the reference wavelength, calculate a first value by nonlinear enhancement correction of the normalized second intensities of the second light beams, calculate a second value by nonlinear reduction correction of the first intensity of the first light beam having the reference wavelength, calculate an evaluation value based on the first value and the second value, and
   output information for navigating a placement position of the optical probe to a suspected position based on the evaluation value.

8. The biomedical examination apparatus of claim 7, wherein the processing circuitry calculates the evaluation value by multiplying the first value and the second value for each of the second intensities detected by the plurality of optical detectors.

9. The biomedical examination apparatus of claim 7, wherein the processing circuitry is configured to perform the nonlinear enhancement correction and the nonlinear reduction correction according to a following equation:
$$M_{(n, Lm)} = K_{(n, Lm)} \cdot D_{(n, Lm)}^{G1} \cdot R_{(n, Lm)}^{G2}$$
where n is a first number of the plurality of the optical detectors, Lm is a second number of the plurality of the light sources, $M_{(n, Lm)}$ is a proximity evaluation value, $K_{(n, Lm)}$ is a weight coefficient, $G_1$ is a first power index for a normalized reference light intensity in terms of reciprocal $D_{(n, Lm)}$ and $G_2$ is a second power index for a normalized light intensity ratio $R_{(n, Lm)}$.

10. The biomedical examination apparatus of claim 9, wherein the processing circuitry sets the first power index $G_1$ to $0<G_1\leq 1$, and sets the second power index $G_2$ to $1<G_2\leq 4$.

11. The biomedical examination apparatus of claim 9, wherein the processing circuitry is configured to calculate the proximity evaluation value by applying weights to normalized light intensities and ratios.

12. The biomedical examination apparatus of claim 7, wherein the evaluation value is a first evaluation value, the processing circuitry is configured to normalize a second evaluation value of a suspected region with a third evaluation value of a healthy region.

* * * * *